United States Patent
Nakajima

(10) Patent No.: US 10,726,553 B2
(45) Date of Patent: Jul. 28, 2020

(54) IMAGE PROCESSING APPARATUS, IMAGE PROCESSING SYSTEM, OPERATION METHOD OF IMAGE PROCESSING APPARATUS, AND COMPUTER-READABLE RECORDING MEDIUM

(71) Applicant: OLYMPUS CORPORATION, Tokyo (JP)

(72) Inventor: Yoshiki Nakajima, Higashiyamato (JP)

(73) Assignee: OLYMPUS CORPORATION, Tokyo (JP)

( * ) Notice: Subject to any disclaimer, the term of this patent is extended or adjusted under 35 U.S.C. 154(b) by 119 days.

(21) Appl. No.: 16/156,003

(22) Filed: Oct. 10, 2018

(65) Prior Publication Data
US 2019/0043196 A1    Feb. 7, 2019

Related U.S. Application Data

(63) Continuation of application No. PCT/JP2017/010150, filed on Mar. 14, 2017.

(30) Foreign Application Priority Data

Jul. 5, 2016    (JP) .................. 2016-133366

(51) Int. Cl.
*G06T 7/00*     (2017.01)
*A61B 1/045*    (2006.01)
(Continued)

(52) U.S. Cl.
CPC ........ *G06T 7/0014* (2013.01); *A61B 1/00009* (2013.01); *A61B 1/00016* (2013.01);
(Continued)

(58) Field of Classification Search
CPC ...... G06K 9/2081; G06K 9/4652; G06K 9/46; G06K 2209/051; G06K 2009/366;
(Continued)

(56) References Cited

U.S. PATENT DOCUMENTS

2007/0078335 A1    4/2007   Horn
2008/0262298 A1    10/2008  Mori
(Continued)

FOREIGN PATENT DOCUMENTS

JP    2003-019111 A    1/2003
JP    2007-167555 A    7/2007
(Continued)

OTHER PUBLICATIONS

International Search Report dated Jun. 13, 2017 issued in International Application No. PCT/JP2017/010150.

*Primary Examiner* — Qian Yang
(74) *Attorney, Agent, or Firm* — Scully, Scott, Murphy & Presser, P.C.

(57) ABSTRACT

An image processing apparatus is configured to acquire a first image group and a second image group and execute image processing on the first and second image groups. The image processing apparatus includes: a processor comprising hardware, wherein the processor is configured to: compare the number of images of interest in the first image group, with the number of images of interest in the second image group; and determine, based on a result of the comparison, priority of processing on the first image group and processing on the second image group.

10 Claims, 18 Drawing Sheets

(51) Int. Cl.
*H04N 7/18* (2006.01)
*G06K 9/46* (2006.01)
*G06K 9/20* (2006.01)
*G06T 7/90* (2017.01)
*A61B 1/00* (2006.01)
*A61B 1/04* (2006.01)
*G06K 9/36* (2006.01)

(52) U.S. Cl.
CPC ............ *A61B 1/041* (2013.01); *A61B 1/045* (2013.01); *G06K 9/2081* (2013.01); *G06K 9/46* (2013.01); *G06K 9/4652* (2013.01); *G06T 7/90* (2017.01); *H04N 7/185* (2013.01); *A61B 1/00059* (2013.01); *G06K 2009/366* (2013.01); *G06K 2209/051* (2013.01); *G06T 2207/10024* (2013.01); *G06T 2207/10068* (2013.01); *G06T 2207/20108* (2013.01); *G06T 2207/30028* (2013.01); *G06T 2207/30092* (2013.01); *G06T 2207/30096* (2013.01)

(58) Field of Classification Search
CPC ........ H04N 7/185; A61B 1/045; A61B 1/041; A61B 1/00016; A61B 1/00009; A61B 1/00059; G06T 7/90; G06T 2207/30092; G06T 2207/30028; G06T 2207/30096; G06T 2207/20108; G06T 2207/10068; G06T 2207/10024
See application file for complete search history.

(56) References Cited

U.S. PATENT DOCUMENTS

| | | |
|---|---|---|
| 2009/0171146 A1 | 7/2009 | Fujita |
| 2010/0130820 A1* | 5/2010 | Shigemori ......... A61B 1/00016 600/109 |
| 2012/0274743 A1 | 11/2012 | Takasugi et al. |
| 2012/0281078 A1* | 11/2012 | Kobayashi ......... A61B 1/00016 348/65 |
| 2013/0190564 A1 | 7/2013 | Fujita |
| 2014/0303435 A1* | 10/2014 | Taniguchi ......... A61B 1/00009 600/103 |
| 2014/0321724 A1* | 10/2014 | Kobayashi ......... A61B 1/00009 382/128 |
| 2015/0031954 A1* | 1/2015 | Kimoto ............ A61B 1/00006 600/118 |

FOREIGN PATENT DOCUMENTS

| | | |
|---|---|---|
| JP | 2012-228532 A | 11/2012 |
| WO | 2012/063623 A1 | 5/2012 |

* cited by examiner

FIG.10

| RECEIVING DEVICE | NUMBER OF IMAGES OF INTEREST |
|---|---|
| 4Aa | 10 |
| 4Ab | 7 |
| 4Ac | 0 |
| 4Ad | 2 |
| 4Ae | 3 |

FIG.11
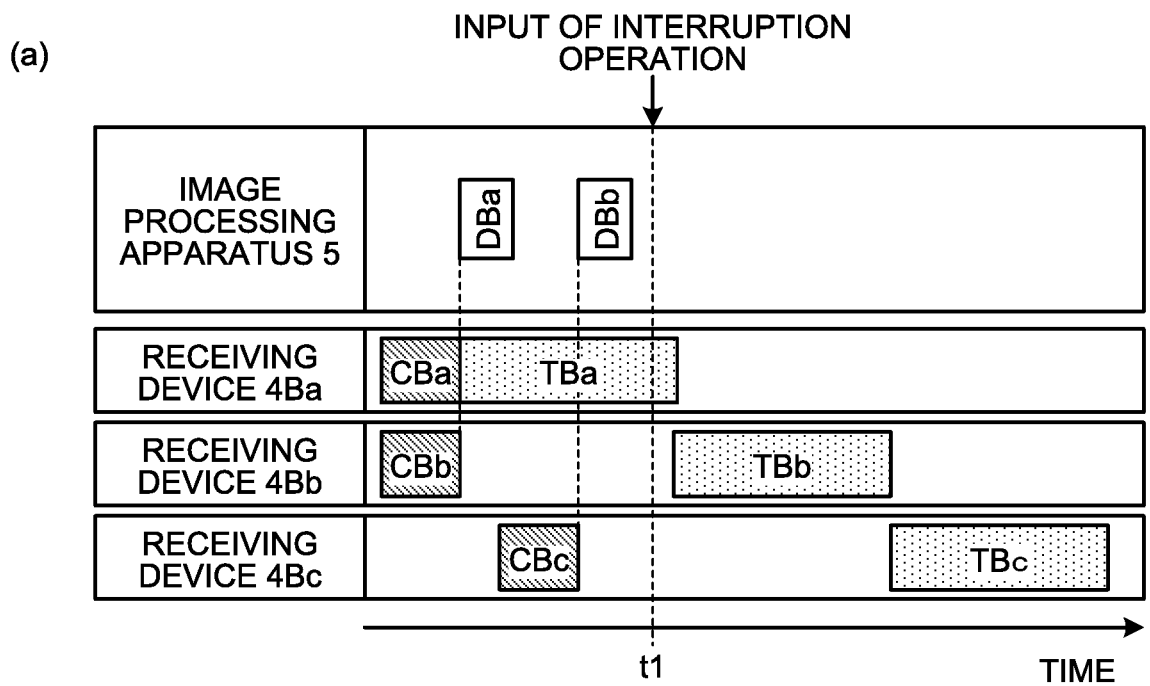
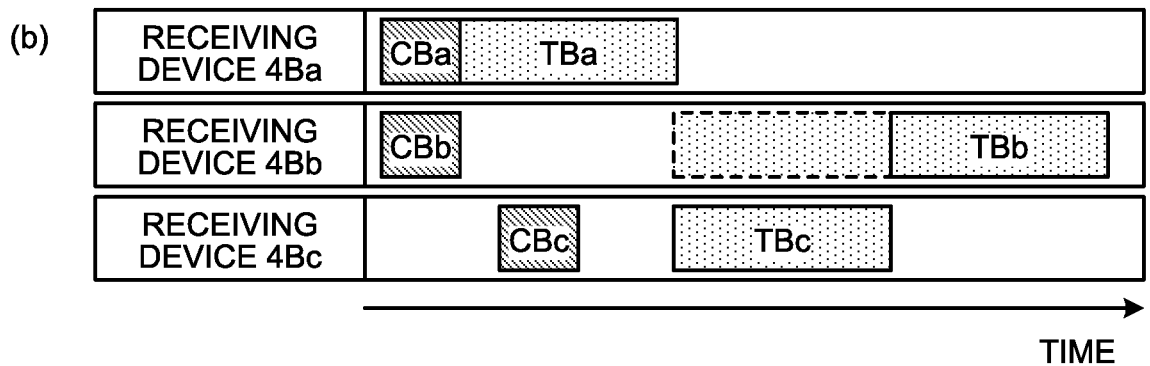

FIG.12
(a)
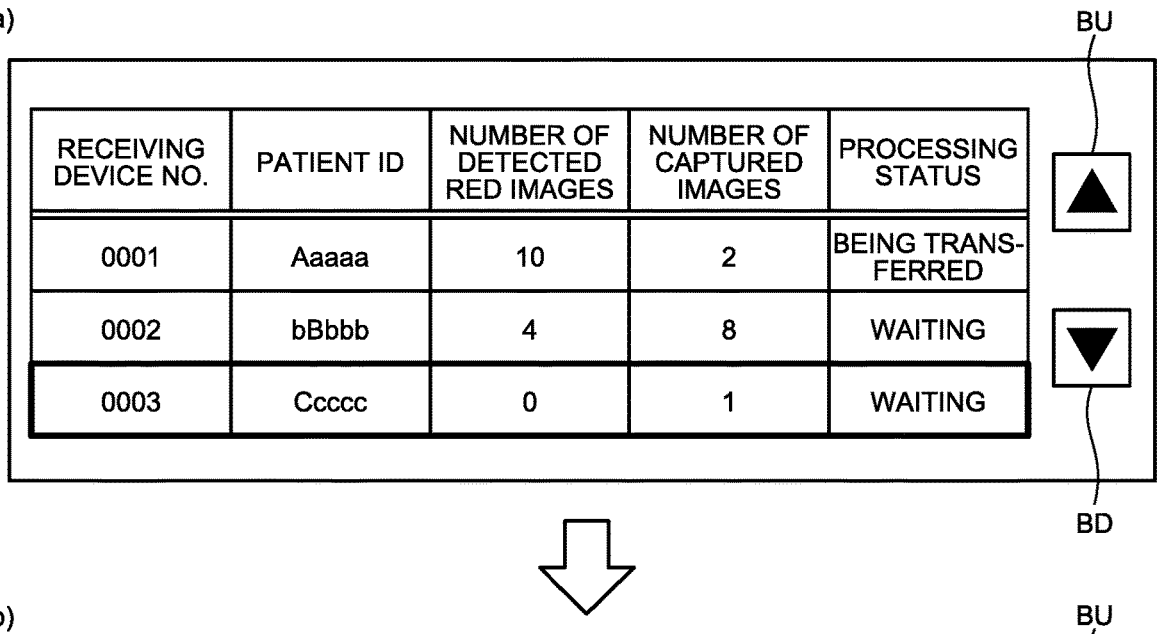
(b)
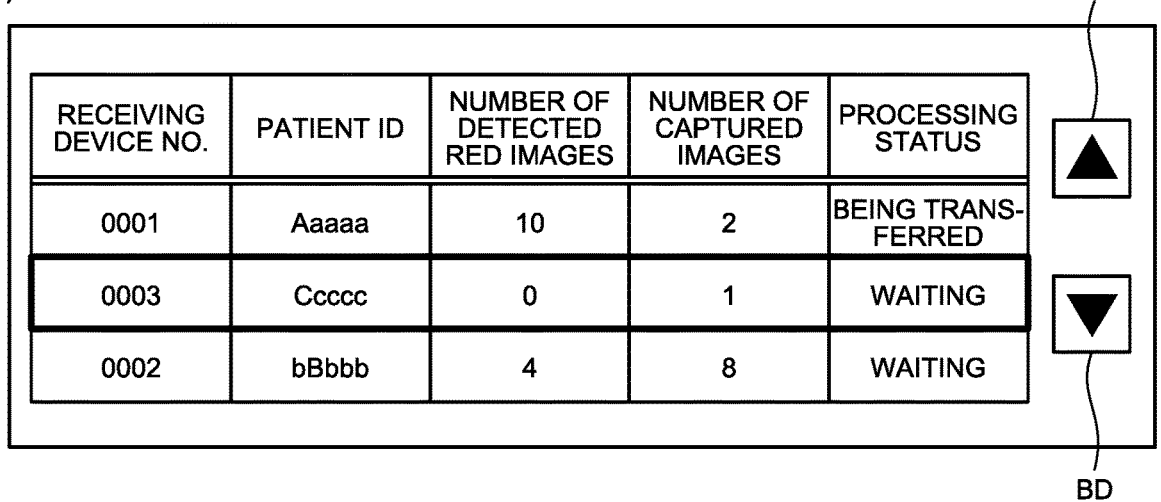

FIG.18

| PRIORITY RANKING | TRANSMISSION RATE [Mbps] |
|---|---|
| 1 | 9 |
| 2 | 7 |
| 3 | 5 |
| 4 | 3 |
| 5 | 2 |
| INITIAL VALUE | 1 |

IMAGE PROCESSING APPARATUS, IMAGE PROCESSING SYSTEM, OPERATION METHOD OF IMAGE PROCESSING APPARATUS, AND COMPUTER-READABLE RECORDING MEDIUM

CROSS-REFERENCE TO RELATED APPLICATION

This application is a continuation of PCT International Application No. PCT/JP2017/010150 filed on Mar. 14, 2017 which claims the benefit of priority from Japanese Patent Application No. 2016-133366 filed on Jul. 5, 2016, the entire contents of which are incorporated herein by reference.

BACKGROUND

1. Technical Field

The present disclosure relates to an image processing apparatus, an image processing system, an operation method of the image processing apparatus, and a computer-readable recording medium.

2. Related Art

In the related art, in the field of endoscopes, capsule type endoscopes, which are body-insertable devices formed in sizes insertable in digestive tracts of subjects, such as patients, have been developed (as seen in, for example, Japanese Unexamined Patent Application, Publication No. 2003-019111). Capsule type endoscopes are devices having imaging functions and wireless communication functions inside capsule-shaped casings; and after being swallowed from mouths of subjects, acquire images by sequentially performing imaging inside organs of the subjects while moving in their digestive tracts by peristaltic movement and the like, and wirelessly transmit the acquired images to receiving devices attached to the subjects. The receiving devices sequentially receive the images transmitted from the capsule type endoscopes, and sequentially cause recording media to record therein the received images. Image processing apparatuses take in the images recorded in the recording media, and cause display devices to display thereon the images that have been subjected to predetermined image processing. By observing the in-vivo images displayed on the display devices, users, such as doctors, make diagnoses of the subjects.

Sometimes, in an examination institute, such as a hospital, plural receiving devices that have been attached to plural subjects are collected all together, and image data of image groups that have been captured are taken in all together by an image processing apparatus from the plural receiving devices. In this case, in a conventional capsule type endoscope system, processing for transmission of the image data of the image groups from the receiving devices to the image processing apparatus, and image processing by the image processing apparatus on the image groups are executed in the order that the receiving devices have been connected to the image processing apparatus.

SUMMARY

In some embodiments, provided is an image processing apparatus configured to acquire a first image group and a second image group and execute image processing on the first and second image groups. The image processing apparatus includes: a processor comprising hardware, wherein the processor is configured to: compare the number of images of interest in the first image group, with the number of images of interest in the second image group; and determine, based on a result of the comparison, priority of processing on the first image group and processing on the second image group.

In some embodiments, provided is an operation method of an image processing apparatus configured to acquire a first image group and a second image group and execute image processing on the first and second image groups. The operation method includes: comparing the number of images of interest in the first image group with the number of images of interest in the second image group; and determining, based on a result of the comparison, priority of processing on the first image group and processing on the second image group.

In some embodiments, provided is a non-transitory computer-readable recording medium with an executable program stored thereon. The program is a program operating an image processing apparatus configured to acquire a first image group and a second image group and execute image processing on the first and second image groups. The operation program causes the image processing apparatus to execute: comparing the number of images of interest in the first image group with the number of images of interest in the second image group; and determining, based on a result of the comparison, priority of processing on the first image group and processing on the second image group.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 10 is a diagram illustrating the number of images of interest transmitted from each receiving device;

FIG. 11 is a diagram for explanation of processing executed by an image processing apparatus according to a modified example 1-3 of the first embodiment;

FIG. 12 is a diagram illustrating an example of an examination list that the image processing apparatus in FIG. 11 causes a display device to display thereon;

FIG. 18 is a diagram illustrating correspondence between priority and transmission rates;

DETAILED DESCRIPTION

Hereinafter, embodiments of an image processing apparatus, an image processing system, an operation method of the image processing apparatus, and an operation program for the image processing apparatus, according to the disclosure will be described, by reference to the drawings. The disclosure is not limited by these embodiments. In the following embodiments, capsule type endoscope systems will be described as examples, but the disclosure is generally applicable to an image processing apparatus that takes in images from plural receiving devices and executes image processing thereon.

Further, the same or corresponding elements are designated with the same reference signs throughout the drawings, as appropriate. Furthermore, the drawings are schematic, and it needs to be noted that the relation among the dimensions of the elements, the ratios among the elements, and the like may be different from the actual ones. Portions having different dimensional relations and ratios among the drawings may be included, too.

First Embodiment

Figure 1:
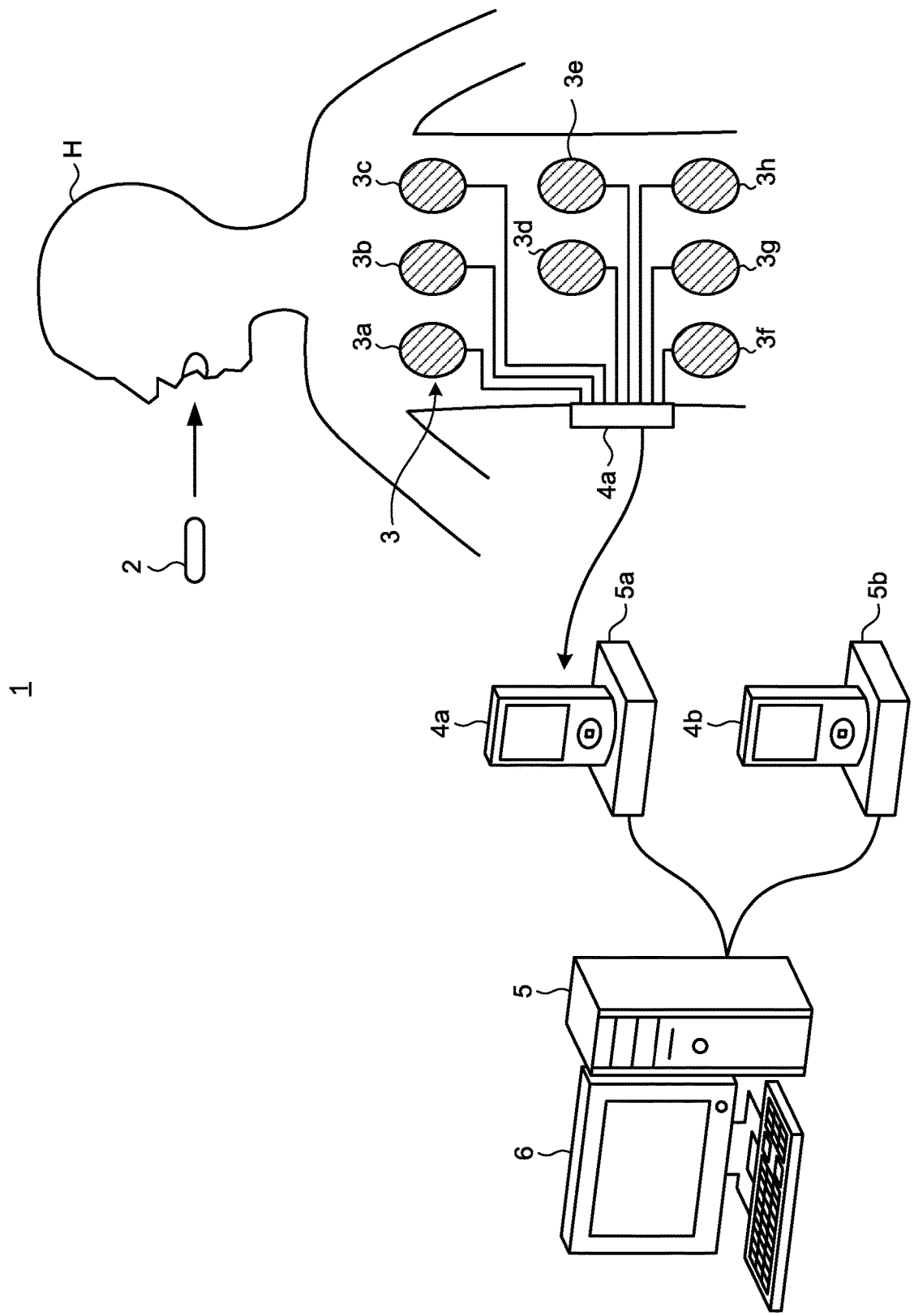
FIG. 1 is a schematic diagram illustrating a schematic configuration of a capsule type endoscope system according to a first embodiment of the disclosure.

FIG. 1 is a schematic diagram illustrating a schematic configuration of a capsule type endoscope system according to a first embodiment of the disclosure. As illustrated in FIG. 1, a capsule type endoscope system 1 according to the first embodiment includes: a capsule type endoscope 2 that acquires an imaging signal by being inserted in a subject H and performs imaging inside the subject H, and transmits the imaging signal by superimposing the imaging signal on a wireless signal; a receiving device 4a serving as a first receiving device that receives, via a receiving antenna unit 3 including plural receiving antennas 3a to 3h attached to the subject H, the wireless signal transmitted from the capsule type endoscope 2, as well as a receiving device 4b serving as a second receiving device; and an image processing apparatus 5 that takes in, via a cradle 5a and a cradle 5b, image data captured by the capsule type endoscope 2, respectively from the receiving device 4a and the receiving device 4b, executes image processing on the image data, and generates in-vivo images. The images generated by the image processing apparatus 5 are output by being displayed on a display device 6, for example. The receiving device 4b receives, via a receiving antenna unit attached to a subject different from that of the receiving device 4a, a wireless signal transmitted from a capsule type endoscope inserted in that different subject, but illustration for this reception is omitted in FIG. 1. Further, each of the receiving device 4a and the receiving device 4b includes a display unit, generates in-vivo images of the subject from the image data captured by the capsule type endoscope, and displays the in-vivo images on the display unit.

Figure 2:
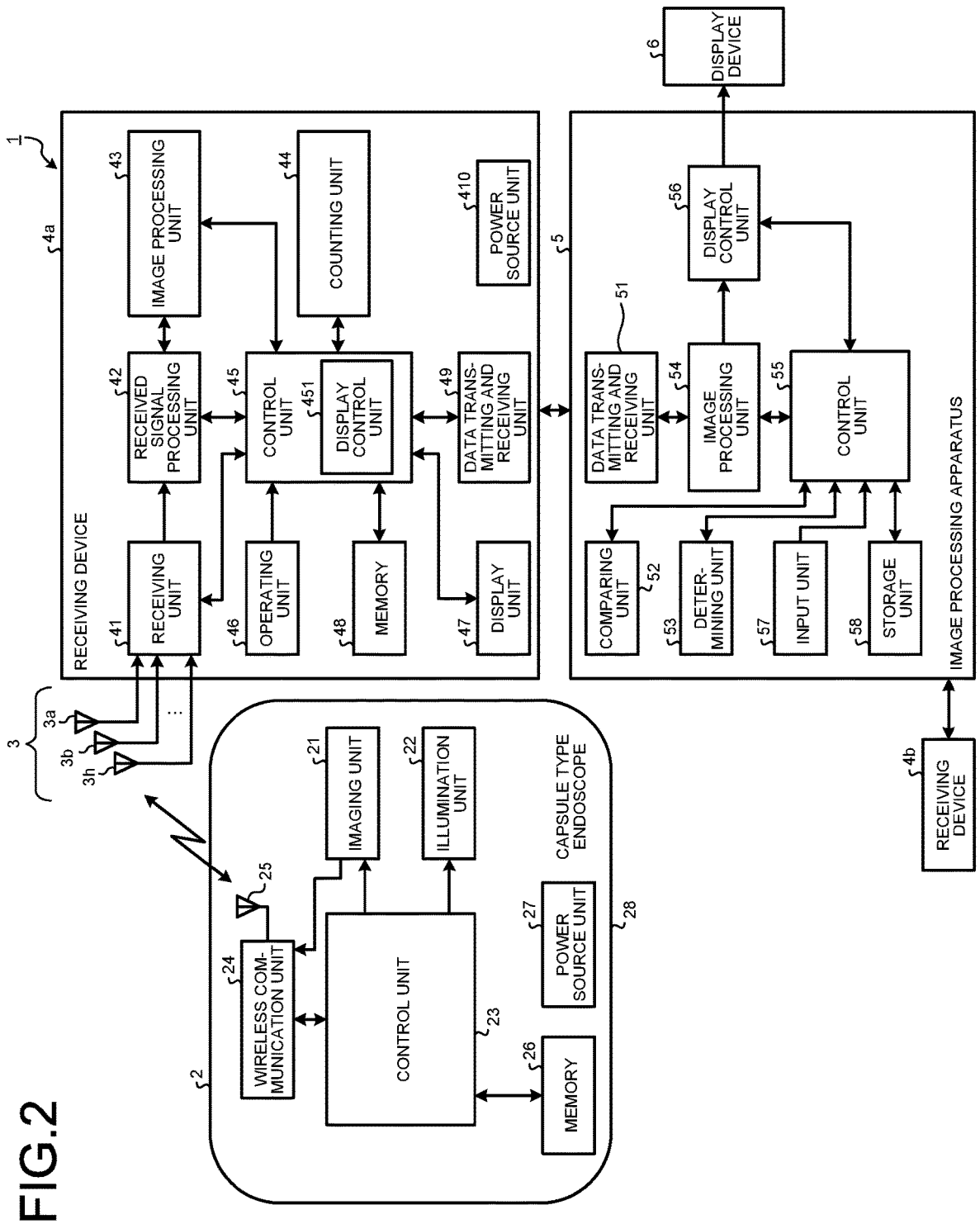
FIG. 2 is a block diagram illustrating a configuration of the capsule type endoscope system illustrated in FIG. 1.

FIG. 2 is a block diagram illustrating a configuration of the capsule type endoscope system illustrated in FIG. 1. As illustrated in FIG. 2, the capsule type endoscope 2 includes an imaging unit 21, an illumination unit 22, a control unit 23, a wireless communication unit 24, an antenna 25, a memory 26, and a power source unit 27. The capsule type endoscope 2 is a device having various parts built in a casing 28 having a size swallowable by the subject H and being capsule-shaped, the various parts including an imaging element.

The imaging unit 21 includes, for example: an imaging element that generates and outputs an imaging signal representing the interior of the subject H from an optical image formed on a light receiving surface; and an optical system, such as an objective lens, which is arranged on a light receiving surface side of the imaging element. The imaging element is formed of a CCD imaging element, or a CMOS imaging element. The imaging unit 21 has plural pixels arranged in a matrix, the plural pixels receiving light from the subject H, and generates an imaging signal by performing photoelectric conversion on the light received by the pixels.

The illumination unit 22 is formed of: a white LED that generates white light that is illumination light; or the like.

The control unit 23 controls operation and processing of each component of the capsule type endoscope 2. The control unit 23 is formed of a processor, such as an application specific integrated circuit (ASIC). When, for example, imaging processing is executed, the control unit 23 controls timing for the imaging unit 21 to execute exposure and reading, and controls the illumination unit 22 to emit the illumination light according to the exposure timing of the imaging unit 21.

The wireless communication unit 24 processes the imaging signal output from the imaging unit 21. The wireless communication unit 24 acquires an imaging signal in a digital format by executing A/D conversion and predetermined signal processing on the imaging signal output from the imaging unit 21, and transmits the imaging signal from the antenna 25 to outside by superimposing the imaging signal, together with related information, on a wireless signal. The related information includes identification information (for example, a serial number) or the like assigned for individual identification of the capsule type endoscope 2.

The memory 26 stores therein an execution program and a control program for the control unit 23 to execute various kinds of operation. Further, the memory 26 temporarily stores therein: the imaging signal that has been subjected to the signal processing in the wireless communication unit 24; and the like. The memory 26 is formed of a random access memory (RAM), a read only memory (ROM); or the like.

The power source unit 27: includes a battery formed of a button battery or the like, a power source circuit that boosts electric power from the battery, and a power switch that switches the power source unit 27 between ON and OFF states; and supplies electric power to each unit in the capsule type endoscope 2 after the power switch is turned ON. The power switch is formed of a reed switch that enables the switch-over between the ON and OFF states by, for example, external magnetic force, and is able to be switched over to the ON state by application of the external magnetic force on the capsule type endoscope 2 before the capsule type endoscope 2 is used (before being swallowed by the subject H).

The casing 28 is an outer casing formed in a size insertable into an organ of the subject H, and liquid-tightly holds therein each component of the capsule type endoscope 2. At least a part of the casing 28 is formed of an optical member that is transparent to light of a predetermined wavelength band, such as visible light, for the imaging unit 21 to perform imaging.

After being swallowed by the subject H, the capsule type endoscope 2 sequentially captures images of parts of a living body (the esophagus, the stomach, the small intestine, the large intestine, and the like) at predetermined cycles (for example, 0.5 second cycles) while moving in the digestive tract of the subject H by peristaltic movement of the organs and the like. The imaging signals and related information acquired by this imaging operation are sequentially transmitted wirelessly to the receiving device 4a.

The receiving device 4a includes a receiving unit 41, a received signal processing unit 42, an image processing unit 43, a counting unit 44, a control unit 45, an operating unit 46, a display unit 47, a memory 48 serving as a first storage unit, a data transmitting and receiving unit 49, and a power source unit 410 that supplies electric power to these units.

The receiving unit 41 receives, via the receiving antenna unit 3 having the plural (eight in FIG. 1) receiving antennas 3a to 3h, the imaging signals and related information wirelessly transmitted from the capsule type endoscope 2. Each of the receiving antennas 3a to 3h is realized by use of, for example, a loop antenna or a dipole antenna, and is arranged at a predetermined position on an outer surface of the subject H.

The received signal processing unit 42 generates image data by performing predetermined signal processing on the imaging signals received by the receiving unit 41. The received signal processing unit 42 is formed of a processor, such as a central processing unit (CPU). The image data generated by the received signal processing unit 42 and the related information are output to the image processing unit 43. The image data referred to herein may be, for example, RAW images, or RGB images.

The image processing unit 43 generates images, based on the image data input from the received signal processing unit 42. The image processing unit 43 outputs images generated by executing optical black (OB) subtraction processing, demosaicing processing, density conversion (gamma conversion or the like) processing, smoothing (noise removal or the like) processing, white balance (WB) adjustment processing, synchronization processing, electronic zooming processing, edge enhancement processing, or the like, on the input image data, correspondingly to a classification or the like of the imaging unit 21. The image processing unit 43 is formed of a processor, such as a CPU.

The counting unit 44 extracts images of interest from the images generated by the image processing unit 43, and counts the number of images of interest extracted. The counting unit 44 is formed of a processor, such as a CPU.

Figure 3:
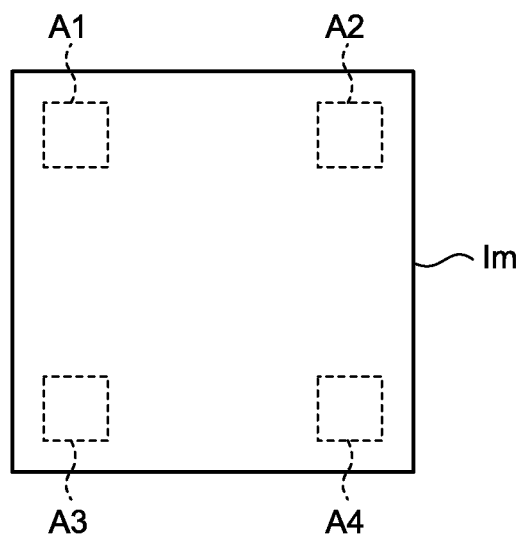
FIG. 3 is a diagram for explanation of an example of a calculation method for an average color of each image.

The images of interest are, for example, red images having large red color components in the images. For example, average values of RGB pixel values for the respective components in an image may be calculated, and if the image has G/R and B/G in predetermined ranges, the image may be defined as a red image. Further, an average color of the whole group of images and an average color of each image may be compared to each other, and if a result of the comparison is in a predetermined range, that image may be defined as a red image. FIG. 3 is a diagram for explanation of an example of a calculation method for an average color of each image. As illustrated in FIG. 3, an average color of each image Im may be defined as an average color of predetermined areas A1 to A4, and in this case, the amount of calculation therefor is able to be reduced as compared to that in calculation of the average color from the entire image Im.

Figure 4:
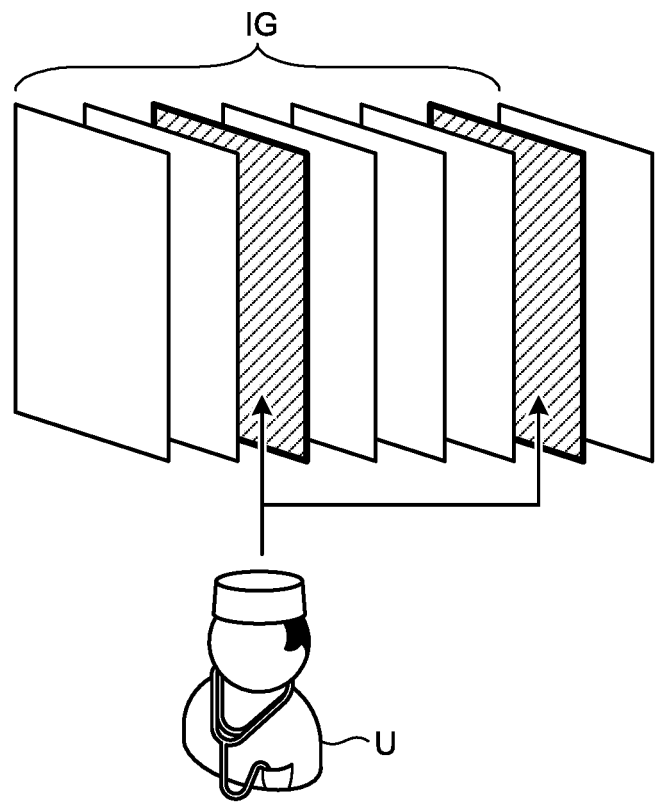
FIG. 4 is a diagram illustrating how a user captures images.

Further, an image of interest may be; a lesion image having a lesioned part detected in the image by predetermined image processing; a feature data detection image that is an image having predetermined feature data calculated from the image, the predetermined feature data being in a predetermined range; or the like. Further, an image of interest may be a captured image captured by a user. FIG. 4 is a diagram illustrating how a user captures images. As illustrated in FIG. 4, a user U observes an image group IG displayed as appropriate during passage of the capsule type endoscope 2 inside the subject H, and captures images from the image group IG, the images having a lesion or the like therein. These captured images are marked, and the user U is able to refer to the captured images as appropriate in later diagnosis. Further, an image of interest may be a selected image selected by a user from a group of images that have been subjected to image processing by the image processing apparatus 5.

The control unit 45 controls each component of the receiving device 4a. The control unit 45 is formed of a processor, such as a CPU. The control unit 45 has a display control unit 451. After executing predetermined processing on a display image generated by the image processing unit 43, the processing being thinning of data according to a display range of the image on the display unit 47, gradation processing, or the like; the display control unit 451 causes the display unit 47 to output the processed display image by displaying the processed display image thereon.

Through the operating unit 46, a user inputs various kinds of setting information and instruction information to the receiving device 4a. The operating unit 46 is an input device, such as, for example, switches or buttons provided on an operation panel of the receiving device 4a.

The display unit 47 displays thereon an in-vivo image or the like based on an image received from the capsule type endoscope 2. The display unit 47 is formed of a liquid crystal display, an organic EL display, or the like. According to control by the display control unit 451, the display unit 47 displays thereon the display image generated by the image processing unit 43. The display unit 47 is formed of a liquid crystal display or the like provided on a principal surface of the receiving device 4a.

The memory 48 stores therein a program for operation of the receiving device 4a and execution of various functions, image data (a first image group) that have been processed by the received signal processing unit 42, the number of images of interest counted by the counting unit 44, related information, and the like. The memory 48 is formed of a RAM, a ROM, or the like.

The data transmitting and receiving unit 49 transmits and receives data when the data transmitting and receiving unit 49 is connected to the image processing apparatus 5 in a state communicatable with the image processing apparatus 5. Specifically, the data transmitting and receiving unit 49 transmits the image data, the number of images of interest, and the related information stored in the memory 48, to the image processing apparatus 5. The data transmitting and receiving unit 49 is formed of a communication I/F, such as a LAN.

This receiving device 4a is attached to and carried by the subject H while imaging is being performed by the capsule type endoscope 2 (for example, while the capsule type endoscope 2 is passing through the digestive tract after being swallowed by the subject H, until the capsule type endoscope 2 is excreted). During this imaging, the receiving device 4a adds, to image data generated from imaging signals received via the receiving antenna unit 3, related information, such as receiving intensity information and receiving time information, in the receiving antennas 3a to 3h, and causes the memory 48 to store therein these image data (the first image group), the number of images of interest, and the related information.

The receiving device 4b may be configured similarly to the receiving device 4a, and thus description thereof will be omitted. A memory (not illustrated) serving as a second storage unit of the receiving device 4b has image data (a second image group) stored therein.

After the imaging by the capsule type endoscope 2 is finished, the receiving device 4a and the receiving device 4b are respectively removed from the subjects, and are respectively set in the cradle 5a and cradle 5b (see FIG. 1) connected to the image processing apparatus 5. Thereby, the receiving device 4a and the receiving device 4b are connected to the image processing apparatus 5 in a state communicatable with the image processing apparatus 5, and transfer (download) the image data (the first and second image groups), the numbers of images of interest, and the related information stored in their respective memories, to the image processing apparatus 5.

The image processing apparatus 5 is configured by use of, for example, a work station including a display device 6a, such as a liquid crystal display. The image processing apparatus 5 includes a data transmitting and receiving unit 51, a comparing unit 52, a determining unit 53, an image processing unit 54, a control unit that integrally controls the respective units, a display control unit 56, an input unit 57, and a storage unit 58.

The data transmitting and receiving unit 51 is an interface connectable to a USB, or a communication line, such as a wired LAN or a wireless LAN, and includes USB ports and a LAN port. The data transmitting and receiving unit 51 is connected to the receiving device 4a and the receiving device 4b respectively via the cradle 5a and the cradle 5b connected to the USB ports, and transmits and receives data to and from the receiving device 4a and the receiving device 4b. Specifically, the data transmitting and receiving unit 51 receives the image data (the first and second image groups), the numbers of images of interest, and the related information transmitted from the receiving device 4a and the receiving device 4b.

The comparing unit 52 compares the number of images of interest in the first image group acquired by the receiving device 4a, with the number of images of interest in the second image group acquired by the receiving device 4b. The comparing unit 52 is formed of a processor, such as a CPU.

The determining unit 53 determines, based on a result of the comparison by the comparing unit 52, priority of processing for transmission of the first image group and second image group from the receiving device 4a and receiving device 4b to the image processing apparatus 5. Specifically, the determining unit 53 determines, based on the result of the comparison by the comparing unit 52, that the image group having the larger number of images of interest has a higher priority. The determining unit 53 is formed of a processor, such as a CPU.

By reading a predetermined program stored in the storage unit 58 described later, the image processing unit 54 executes predetermined image processing for generating in-vivo images corresponding to imaging signals input from the data transmitting and receiving unit 51 or imaging signals stored in the storage unit 58. The image processing unit 54 is formed of a processor, such as a CPU.

By reading various programs stored in the storage unit 58, a control unit 55 executes, based on signals input via the input unit 57 and data and the like input from the data transmitting and receiving unit 51, transfer or the like of instructions and data to the respective units forming the image processing apparatus 5, and integrally controls operation of the whole image processing apparatus 5. Further, based on the priority determined by the determining unit 53, the control unit 55 executes control of causing the receiving device 4a and the receiving device 4b to respectively transmit images of the first image group and second image group. Further, based on the priority determined by the determining unit 53, the control unit 55 executes control of causing the image processing unit 54 to execute image processing on the first image group and second image group. The control unit 55 is formed of a processor, such as a CPU.

After executing predetermined processing on an image generated by the image processing unit 54, the processing being thinning of data according to a display range of the image on the display device 6, gradation processing, or the like, the display control unit 56 causes the display device 6 to output the processed image by displaying the processed image. The display control unit 56 is formed of a processor, such as a CPU.

The input unit 57 receives input of information and instructions according to a user's operations. The input unit 57 is formed of an input device, such as a keyboard and a mouse, a touch panel, or various switches.

The storage unit 58 stores therein: a program for operation of the image processing apparatus 5 and execution of various functions; various kinds of information used in the execution of the program; and the images, the numbers of images of interest, the related information, and the like acquired via the receiving device 4a and receiving device 4b. The storage unit 58 is formed of a semiconductor memory, such as a flash memory, a RAM, or a ROM; or a recording medium, such as an HDD, an MO, a CD-R, or a DVD-R, as well as a drive device or the like that drives the recording medium.

Figure 5:
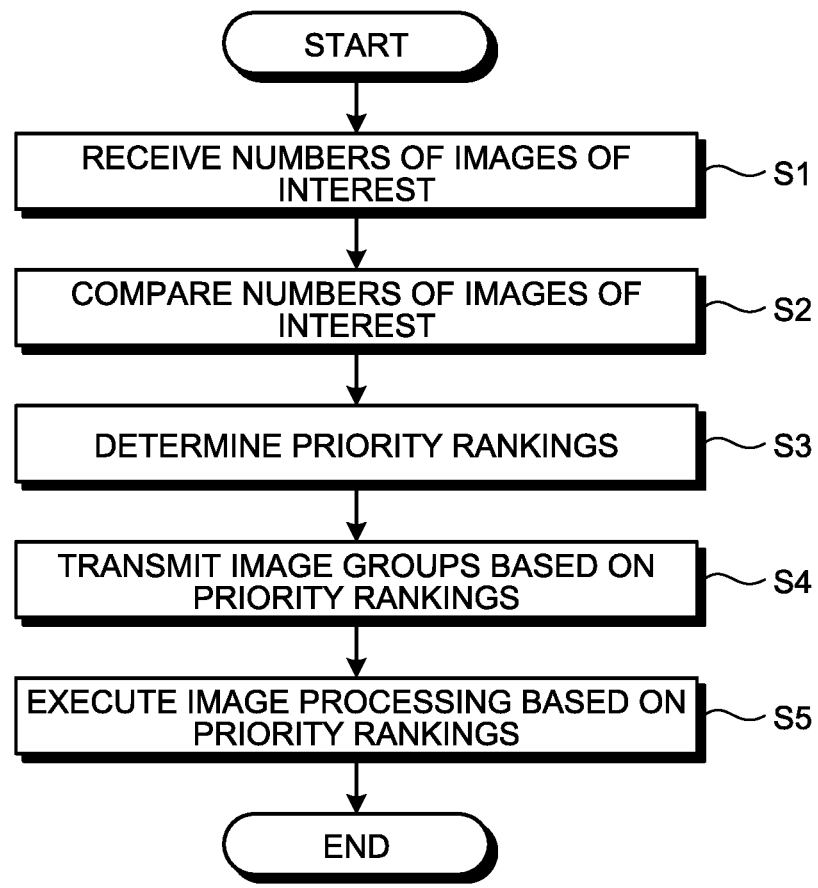
FIG. 5 is a flow chart illustrating a procedure of processing executed by an image processing apparatus illustrated in FIG. 2.
Figure 6:
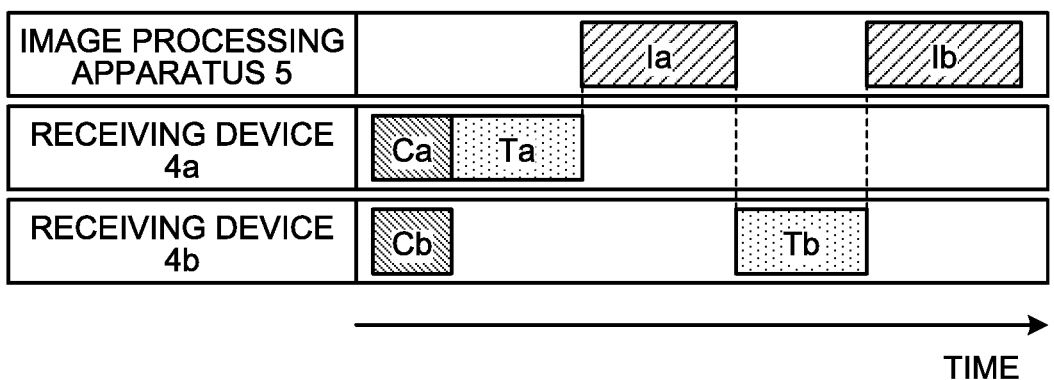
FIG. 6 is a diagram for explanation of the flow chart in FIG. 5.

Next, processing executed by the image processing apparatus 5 will be described, the processing being in a case where the receiving device 4a and the receiving device 4b are connected to the image processing apparatus 5 via the cradle 5a and the cradle 5b, substantially at the same time. FIG. 5 is a flow chart illustrating a procedure of processing executed by the image processing apparatus illustrated in FIG. 2. FIG. 6 is a diagram for explanation of the flow chart in FIG. 5. In FIG. 6, processing executed by each unit of the capsule type endoscope system 1 has been designated with a reference sign. As illustrated in FIG. 5 and FIG. 6, firstly, the image processing apparatus 5 executes processing (Ca) of receiving the number of images of interest, from the receiving device 4a, and executes processing (Cb) of receiving the number of images of interest, from the receiving device 4b (Step S1).

Subsequently, the comparing unit 52 compares the number of images of interest from the receiving device 4a, with the number of images of interest from the receiving device 4b (Step S2).

The determining unit 53 determines, based on a result of the comparison by the comparing unit 52, priority of processing for transmission of the image groups by the receiving device 4a and the receiving device 4b (Step S3). Specifically, the determining unit 53 determines that the processing for transmission of the first image group by the receiving device 4a has a higher priority, if the number of images of interest from the receiving device 4a is larger.

Based on the priority determined by the determining unit 53, the control unit 55 executes control of causing the receiving device 4a and the receiving device 4b to respectively transmit the first image group and the second image group (Step S4). Specifically, if the determining unit 53 determines that the priority of the processing for transmission of the first image group by the receiving device 4a is higher, the control unit 55 executes, by transmitting a control signal to the receiving device 4a, processing (Ta) of preferentially causing the receiving device 4a to transmit the first image group.

Further, based on the priority determined by the determining unit 53, the control unit 55 executes control of causing the image processing unit 54 to execute image processing on the first image group and the second image group (Step S5). Specifically, if the determining unit 53 determines that the priority of image processing on the first image group from the receiving device 4a is higher, the control unit 55 causes the image processing unit 54 to execute image processing (Ia) on the first image group having the higher priority. When the image processing (Ia) is finished, a user is able to observe the first image group having the higher priority and make a diagnosis.

Thereafter, by transmitting a control signal to the receiving device 4b, the control unit 55 executes processing (Tb) of causing the receiving device 4b to transmit the second image group having the lower priority. Furthermore, the control unit 55 causes the image processing unit 54 to execute image processing (Ib) on the second image group. The series of processing is then ended.

As described above, according to the first embodiment, an image processing apparatus, which enables a user to observe image groups in descending order of priority by preferentially executing processing on an image group having many images of interest, is able to be realized.

It is now assumed that the images of interest are red images. The red images correspond to images indicating possibility of hemorrhage in subjects. In this case, a user is able to preferentially make a diagnosis of a subject that may be bleeding, and perform treatment, such as hemostasis, early. Further, it is now assumed that the images of interest are lesion images. The lesion images are images resulting from predetermined image processing and indicating possibility of predetermined lesions. In this case, a user is able to preferentially make a diagnosis of a subject that may have a lesion, and perform treatment of the lesion early. As described above, by change of setting of the images of interest, a user is able to perform a desired treatment early. Furthermore, it is now assumed that the images of interest are captured images. The captured images are images of lesions or the like, of which a user desires to make diagnoses in detail later. In this case, a user is able to preferentially make a diagnosis of a subject, for which an image group has been taken, the image group having many images captured by the user.

With respect to the first embodiment above, the configuration, in which the receiving device 4a includes the counting unit 44, has been described, but the first embodiment is not limited to this configuration. For example, the image processing apparatus 5 may include a counting unit; and this counting unit of the image processing apparatus 5 may be configured to count the numbers of images of interest after the image processing apparatus 5 receives the first image group and the second image group from the receiving device 4a and the receiving device 4b, and the image processing unit 54 may be configured to execute image processing in the order of priority based on the counted numbers of images of interest.

Further, with respect to the first embodiment above, the case where the receiving device 4a and the receiving device 4b are connected to the image processing apparatus 5 via the cradle 5a and the cradle 5b substantially at the same time has been described, but practically, the receiving device 4a and the receiving device 4b may be connected to the image processing apparatus 5 at different timings. In that case, a configuration, in which connection of the other receiving device is delayed for a predetermined time period after a receiving device is connected to the image processing apparatus 5, may be adopted. Specifically, if a receiving device is connected to the image processing apparatus 5, and another receiving device is connected to the image processing apparatus 5 within the predetermined time period, processing may be executed as if these receiving devices have been connected to the image processing apparatus 5 at the same time. On the contrary, if a receiving device is connected to the image processing apparatus 5, and another receiving device is not connected to the image processing apparatus 5 within the predetermined time period, processing may be started only with the receiving device that is connected to the image processing apparatus 5.

Modified Examples 1-1

Figure 7:
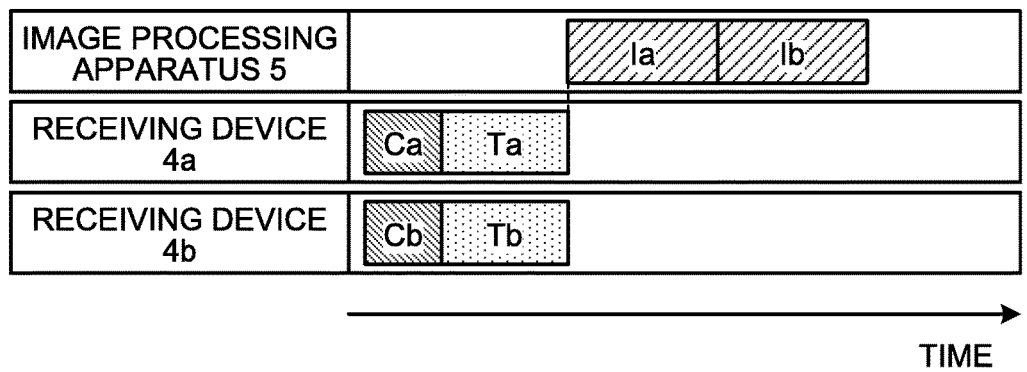
FIG. 7 is a diagram for explanation of processing executed by an image processing apparatus according to a modified example 1-1 of the first embodiment.

FIG. 7 is a diagram for explanation of processing executed by an image processing apparatus according to a modified example 1-1 of the first embodiment. As illustrated in FIG. 7, if data are able to be transmitted concurrently from plural receiving devices, a first image group and a second image group may be respectively transmitted from the receiving device 4a and the receiving device 4b in parallel with each other.

In this case, the control unit 55 executes control of causing the image processing unit 54 to execute image processing on the first image group and the second image group based on priority determined by the determining unit 53. Specifically, if the determining unit 53 determines that the priority of image processing on the first image group from the receiving device 4a is higher, the control unit 55 causes the image processing unit 54 to execute image processing (Ia) on the first image group having the higher priority. Thereafter, the control unit 55 causes the image processing unit 54 to execute image processing (Ib) on the second image group.

Modified Examples 1-2

Figure 8:
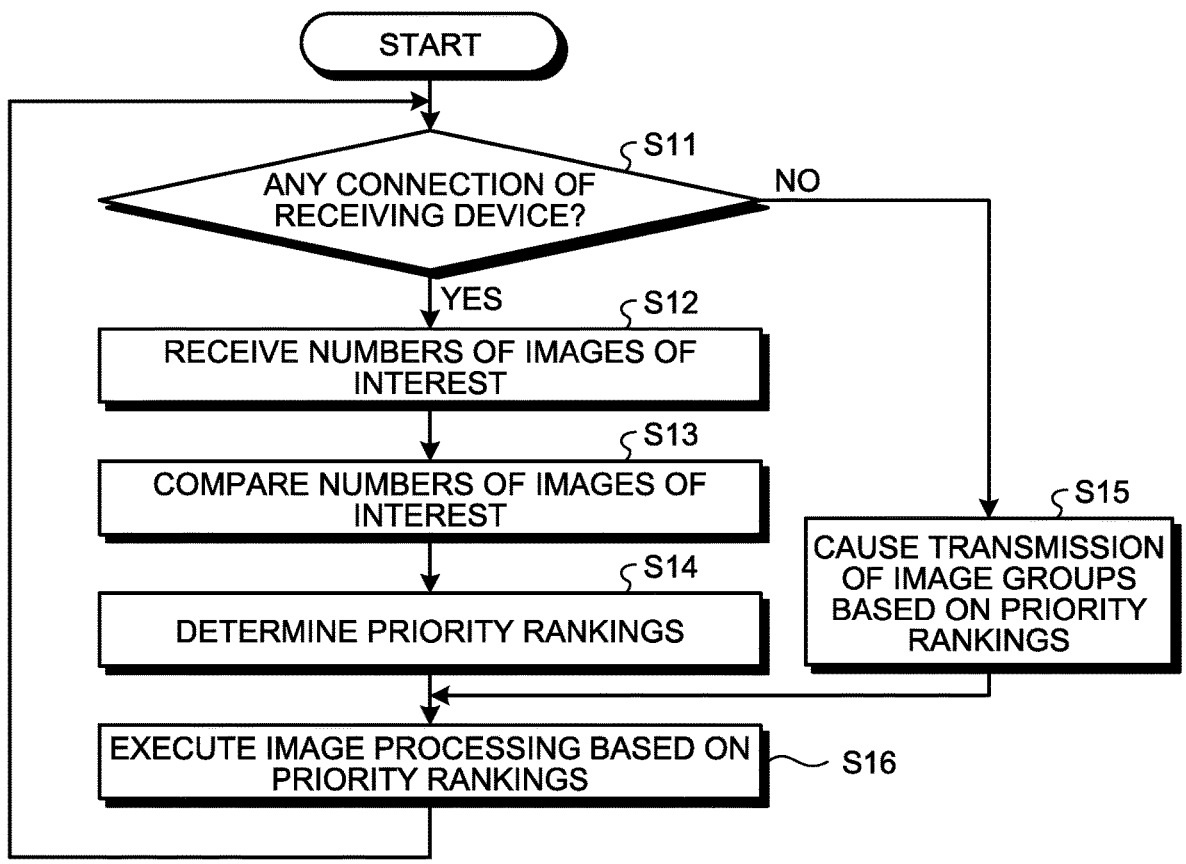
FIG. 8 is a flow chart illustrating a procedure of processing executed by an image processing apparatus according to a modified example 1-2 of the first embodiment.
Figure 9:
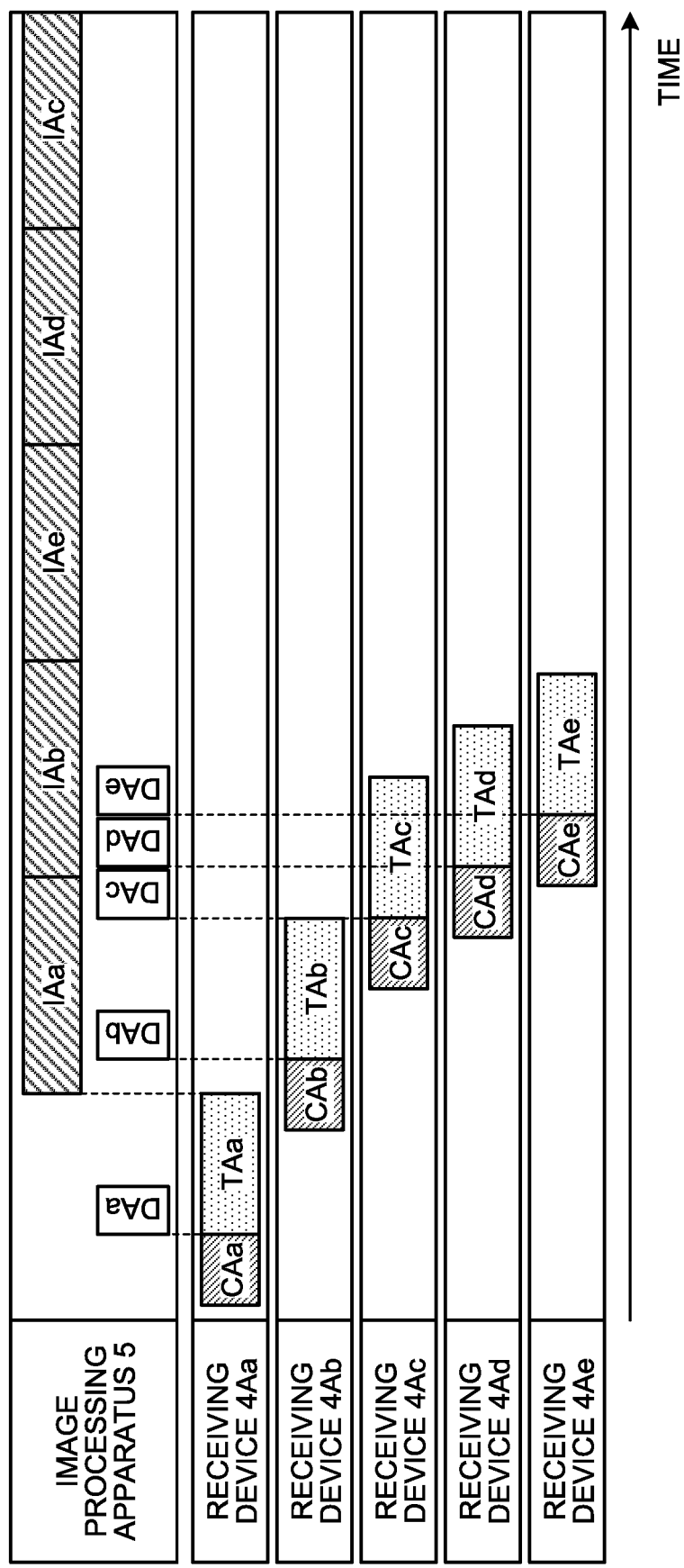
FIG. 9 is a diagram for explanation of the flow chart in FIG. 8.

FIG. 8 is a flow chart illustrating a procedure of processing executed by an image processing apparatus according to a modified example 1-2 of the first embodiment. FIG. 9 is a diagram for explanation of the flow chart in FIG. 8. As illustrated in FIG. 9, in this configuration, image groups are respectively transmitted from receiving devices 4Aa to 4Ae to the image processing apparatus 5. The receiving devices 4Aa to 4Ae may be configured similarly to the receiving device 4*a*.

As illustrated in FIG. 8 and FIG. 9, firstly, the control unit 55 of the image processing apparatus 5 determines whether or not a receiving device has been connected to the image processing apparatus 5 (Step S11). If it is determined that a receiving device has not been connected to the image processing apparatus 5 (Step S11: No), the procedure is advanced to Step S15 described later, and the image processing that has been executed till then is continuously executed.

On the contrary, if it is determined that a receiving device has been connected to the image processing apparatus 5 (Step S11: Yes), processing (CAa) for reception of the number of images of interest from the receiving device 4Aa that has been connected to the image processing apparatus 5 first is executed (Step S12).

When this processing is completed, the comparing unit 52 of the image processing apparatus 5 compares the received numbers of images of interest from the receiving devices with one another (Step S13).

Further, the determining unit 53 executes processing (DAa) of determining, based on a result of the comparison by the comparing unit 52, priority for image processing on image groups transmitted from the receiving devices (Step S14). Since only one receiving device has been connected to the image processing apparatus 5, image processing on the image group received from the receiving device 4Aa is determined to be executed preferentially.

Further, in parallel with Steps S13 and S14, the image processing apparatus 5 executes processing (TAa) of causing the receiving device 4Aa to transmit the image group (Step S15).

When the processing (TAa) of Step S15 is completed, the image processing apparatus 5 executes, based on the priority determined by the determining unit 53, image processing (IAa) on the image group received from the receiving device 4Aa (Step S16).

Thereafter, the procedure is returned to Step S11, and the processing is repeated.

Subsequently, the receiving device 4Ab is connected to the image processing apparatus 5. The image processing apparatus 5 then determines that a receiving device has been connected to the image processing apparatus 5 (Step S11: Yes), and executes processing (CAb) of receiving the number of images of interest from the receiving device 4Ab (Step S12).

When this processing is completed, the comparing unit 52 of the image processing apparatus 5 compares the received numbers of images of interest from the receiving devices with one another (Step S13).

Further, the determining unit 53 executes processing (DAb) of determining, based on a result of the comparison by the comparing unit 52, priority for image processing on image groups transmitted from the receiving devices (Step S14). Since the image processing (IAa) on the image group received from the receiving device 4Aa has been started already, the image processing (IAa) is not included in the determination. As a result, the determining unit 53 determines that image processing (IAb) on the image group to be received from the receiving device 4Ab has a high priority.

Further, in parallel with Steps S13 and S14, the image processing apparatus 5 executes processing (TAb) of causing the receiving device 4Ab to transmit the image group (Step S15).

The image processing apparatus 5 then executes image processing based on the priority (Step S16).

Further, the receiving device 4Ac is connected to the image processing apparatus 5. The image processing apparatus 5 then determines that a receiving device has been connected to the image processing apparatus 5 (Step S11: Yes), and executes processing (CAc) of receiving the number of images of interest from the receiving device 4Ac (Step S12).

When this processing is completed, the comparing unit 52 of the image processing apparatus 5 compares the received numbers of images of interest from the respective receiving devices with one another (Step S13).

Further, the determining unit 53 executes processing (DAc) of determining, based on a result of the comparison by the comparing unit 52, priority for image processing on image groups transmitted from the receiving devices (Step S14). Since the image processing (IAb) on the image group received from the receiving device 4Ab has been started already at the time of processing (DAc) as illustrated in FIG. 9, the image processing (IAb) is not included in the determination. As a result, the determining unit 53 determines that image processing (IAc) on the image group to be received from the receiving device 4Ac has a high priority.

Subsequently, the receiving device 4Ad is connected to the image processing apparatus 5. The image processing apparatus 5 then determines that a receiving device has been connected to the image processing apparatus 5 (Step S11: Yes), and executes processing (CAd) of receiving the number of images of interest from the receiving device 4Ad (Step S12).

When this processing is completed, the comparing unit 52 of the image processing apparatus 5 compares the received numbers of images of interest from the receiving devices with one another (Step S13).

Further, the determining unit 53 executes processing (DAd) of determining, based on a result of the comparison by the comparing unit 52, priority for image processing on image groups transmitted from the receiving devices (Step S14). Since the image processing (IAb) on the image group received from the receiving device 4Ab has been started already at the time of the processing (DAd) as illustrated in FIG. 9, the image processing (IAb) is not included in the determination. Priority of image processing on image groups from the receiving device 4Ac and the receiving device 4Ad, for which image processing has not been started, are respectively determined.

FIG. 10 is a diagram illustrating the number of images of interest transmitted from each receiving device. The comparing unit 52 compares the number of images of interest from the receiving device 4Ac and the number of images of interest from the receiving device 4Ad with each other. Since the number of images of interest from the receiving device 4Ac is zero, and the number of images of interest from the receiving device 4Ad is two; it is understood that the numbers of images of interest are in a relation, "receiving device 4Ad>receiving device 4Ac". Based on this result of the comparison by the comparing unit 52, the determining unit 53 determines the priority of the image processing on the image group from the receiving device 4Ad having the larger number of images of interest as first, and the priority of the image processing on the image group from the receiving device 4Ac as second.

Further, in parallel with Steps S13 and S14, the image processing apparatus 5 executes processing (TAd) of causing the receiving device 4Ad to transmit the image group (Step S15).

Further, the receiving device 4Ae is connected to the image processing apparatus 5. The image processing apparatus 5 then determines that a receiving device has been connected to the image processing apparatus 5 (Step S11: Yes), and executes processing (CAe) of receiving the number of images of interest from the receiving device 4Ae (Step S12).

When this processing is completed, the comparing unit 52 of the image processing apparatus 5 compares the received numbers of images of interest from the receiving devices with one another (Step S13).

Further, the determining unit 53 executes processing (DAe) of determining, based on a result of the comparison by the comparing unit 52, priority for image processing on image groups transmitted from the receiving devices (Step S14). Since the image processing (IAb) on the image group received from the receiving device 4Ab has been started already at the time of the processing (DAe) as illustrated in FIG. 9, the image processing (IAb) is not included in the determination. Priority of image processing on image groups from the receiving device 4Ac, the receiving device 4Ad, and the receiving device 4Ae for which image processing has not been started, are respectively determined.

As illustrated in FIG. 10, the comparing unit 52 compares the number of images of interest from the receiving device 4Ac, the number of images of interest from the receiving device 4Ad, and the number of images of interest from the receiving device 4Ae, with one another. Since the number of images of interest from the receiving device 4Ac is zero, the number of images of interest from the receiving device 4Ad is two, and the number of images of interest from the receiving device 4Ae is three, it is understood that the numbers of images of interest are in a relation, "receiving device 4Ae>receiving device 4Ad>receiving device 4Ac". Based on this result of the comparison by the comparing unit 52, the determining unit 53 determines the priority of the image processing on the image group from the receiving device 4Ae having the largest number of images of interest as first, the priority of the image processing on the image group from the receiving device 4Ad having the second largest number of images of interest as second, and the priority of the image processing on the image group from the receiving device 4Ac as third. As a result, when the image processing (IAb) on the image group received from the receiving device 4Ab is completed in the image processing apparatus 5, based on the priority, image processing (IAe) on the image group received from the receiving device 4Ae is started, as illustrated in FIG. 9 (Step S16).

In parallel with Steps S13 and S14, the image processing apparatus 5 executes processing (TAe) of causing the receiving device 4Ae to transmit the image group (Step S15). If the processing (TAe) of causing the receiving device 4Ae to transmit the image group has not been completed when the image processing (IAb) on the image group received from the receiving device 4Ab is completed, the image processing (IAe) may be executed after completion of the processing (TAe) is waited for, but image processing (IAd) on the image group received from the receiving device 4Ad with the second highest priority may be executed by change of the priority.

Further, as illustrated in FIG. 9, when the image processing (IAe) on the image group received from the receiving device 4Ae is completed in the image processing apparatus 5, based on the priority, the image processing (IAd) on the image group received from the receiving device 4Ad is started, as illustrated in FIG. 9 (Step S16).

Lastly, when the image processing (IAd) on the image group received from the receiving device 4Ad is completed in the image processing apparatus 5, the image processing (IAc) on the image group received from the receiving device 4Ac is started, based on the priority (Step S16).

When the image processing (IAc) on the image group received from the receiving device 4Ac is completed, the series of processing is ended.

As described above, according to the modified example 1-2 of the first embodiment, since image processing on an image group from the receiving device 4Ae with many images of interest is completed first, a user is able to observe image groups in descending order of priority.

Modified Examples 1-3

FIG. 11 is a diagram for explanation of processing executed by an image processing apparatus according to a modified example 1-3 of the first embodiment. As illustrated in FIG. 11, in this configuration, image groups are respectively transmitted from receiving devices 4Ba to 4Bc to the image processing apparatus 5. The receiving devices 4Ba to 4Bc may be configured similarly to the receiving device 4a.

As illustrated in (a) of FIG. 11, firstly, processing (CBa and CBb) for reception of the numbers of images of interest from the receiving device 4Ba and the receiving device 4Bc is executed. Further, processing (DBa) for determination of priority of processing for transmission of image groups from the receiving device 4Ba and the receiving device 4Bb to the image processing apparatus 5 is executed. Specifically, the determining unit 53 determines the priority of processing (TBa) for transmission of the image group from the receiving device 4Ba with the larger number of detected red images that are images of interest to be higher. The processing (TBa) for transmission of the image group from the receiving device 4Ba determined to have the higher priority is then executed. Thereafter, the receiving device 4Bc is connected to the image processing apparatus 5, and processing (CBc) for reception of the number of images of interest from the receiving device 4Bc is executed. Further, processing (DBb) of the determining unit 53 determining priority of processing for transmission of image groups from the receiving device 4Bb and receiving device 4Bc to the image processing apparatus 5 is executed. Specifically, the determining unit 53 determines the priority of processing (TBb) for transmission of the image group from the receiving device 4Bb with the higher number of detected red images that are images of interest to be higher.

FIG. 12 is a diagram illustrating an example of an examination list that the image processing apparatus in FIG. 11 causes a display device to display thereon. (a) of FIG. 12 is an example of the examination list being displayed on the display device 6 at a time t1 illustrated in FIG. 11. As illustrated in FIG. 12, on the display device 6, numbers for the receiving devices, IDs of patients who have been attached with these receiving devices, the numbers of detected red images that are images of interest, the numbers of captured images, processing statuses, and the like are displayed.

At the time t1, the receiving device 4Ba corresponding to a receiving device No. 0001 is executing the processing (TBa) of transmitting (transferring) images. Between the receiving device 4Bb corresponding to a receiving device No. 0002 and the receiving device 4Bc corresponding to a receiving device No. 0003, the priority of the receiving device 4Bb with the larger number of detected red images that are images of interest has been determined to be higher. Since processing with a higher priority is displayed up in the examination list of FIG. 12 on the screen, as illustrated in (a) of FIG. 12, the receiving device No. 0002 is displayed above the receiving device No. 0003.

If a user desires to observe the image group from the receiving device 4Bc first, the user inputs an interruption operation for switching between positions of the receiving device 4Bb and the receiving device 4Bc on the screen by selecting the receiving device No. 0003 on the screen of (a) of FIG. 12 and using an up button BU or a down button BD on the right side of the screen. The receiving device No. 0003 is then displayed above the receiving device No. 0002, as illustrated in (b) of FIG. 12. What is more, as illustrated in (b) of FIG. 11, the processing (TBc) for transmission of the image group from the receiving device 4Bc is executed preferentially to the processing (TBb) for transmission of the image group from the receiving device 4Bb.

As described above, a configuration enabling switch-over between the priority determined by the determining unit 53 through an interruption operation by a user may be adopted. As illustrated in FIG. 12, since the numbers of detected red images and the numbers of captured images are displayed on the display device 6, the user is able to change the priority based on these pieces of information.

Modified Examples 1-4

Figure 13:
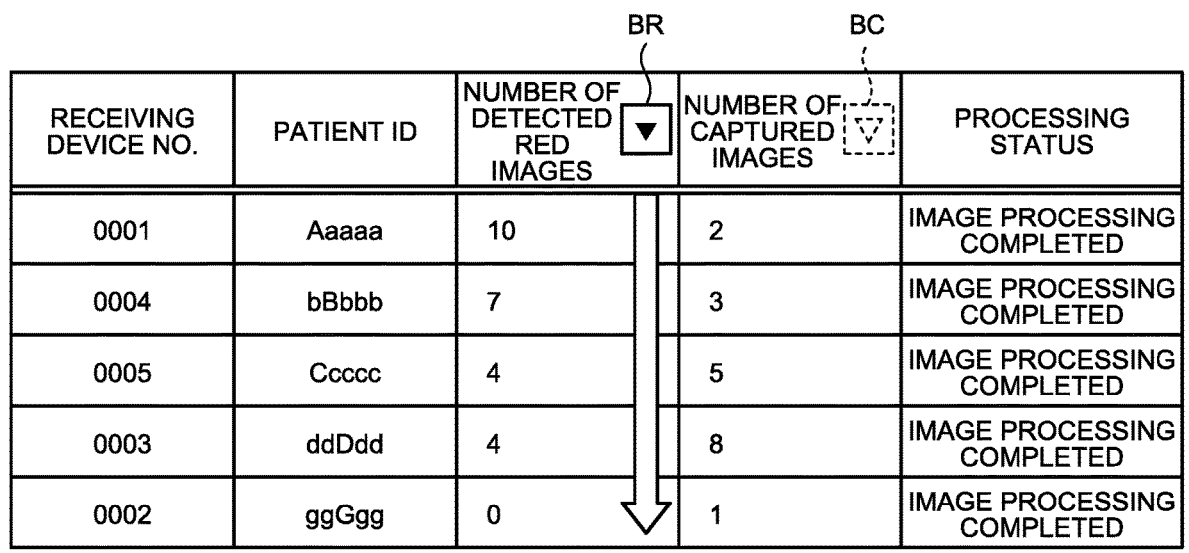
FIG. 13 is a diagram illustrating an example of an examination list that an image processing apparatus according to a modified example 1-4 of the first embodiment causes a display device to display thereon.

FIG. 13 is a diagram illustrating an example of an examination list that an image processing apparatus according to a modified example 1-4 of the first embodiment causes a display device to display thereon. FIG. 13 illustrates an example of the examination list being displayed on the display device 6 in a state where the series of image processing (IAa) to (IAe) has finished in the modified example 1-2. In FIG. 13 also, similarly to FIG. 12, receiving device numbers, patient IDs, the numbers of detected red images, the numbers of captured images, processing statuses, and the like are displayed on the display device 6.

As illustrated in FIG. 13, image groups, on which image processing has finished, are displayed in lines. By use of sort buttons BR and BC for the numbers of detected red images and the numbers of captured images, the image groups are able to be sorted according to either of these numbers. FIG. 13 illustrates a state where the image groups have been sorted in descending order of the numbers of detected red images. As a result, a user is able to observe from the image group having the largest number of detected red images or captured images.

FIG. 13 illustrates the case where only the image groups, on which image processing has finished, are displayed. In this case, a user: is able to know image groups that are able to be observed, and the numbers of detected red images and the numbers of captured images in those image groups; and is able to obtain information for determining from which image group the user is to start observation.

Second Embodiment

Figure 14:
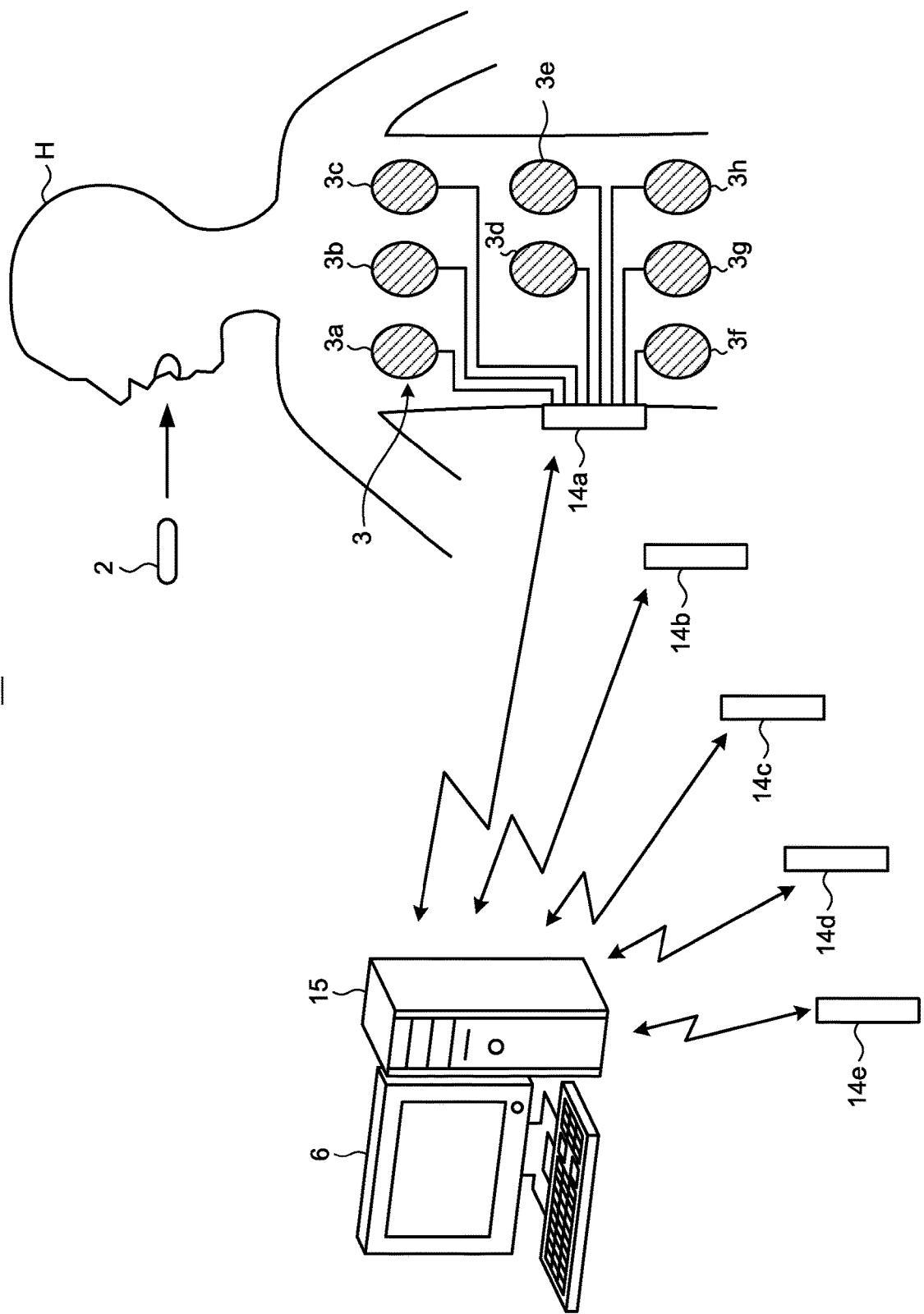
FIG. 14 is a schematic diagram illustrating a schematic configuration of a capsule type endoscope system according to a second embodiment of the disclosure.

FIG. 14 is a schematic diagram illustrating a schematic configuration of a capsule type endoscope system according to a second embodiment of the disclosure. As illustrated in FIG. 14, in a capsule type endoscope system 11, receiving devices 14a to 14e are connected to an image processing apparatus 15 via wireless communication. Description of configurations similar to those of the first embodiment will be omitted as appropriate. In this capsule type endoscope system 11, imaging signals captured by the capsule type endoscope 2 are transmitted to the receiving device 14a in real time. Further, the receiving device 14a generates image data by executing image processing or the like on the received imaging signals in the order of reception, and starts transmission of the image data to the image processing apparatus 15 in the order of generation.

Figure 15:
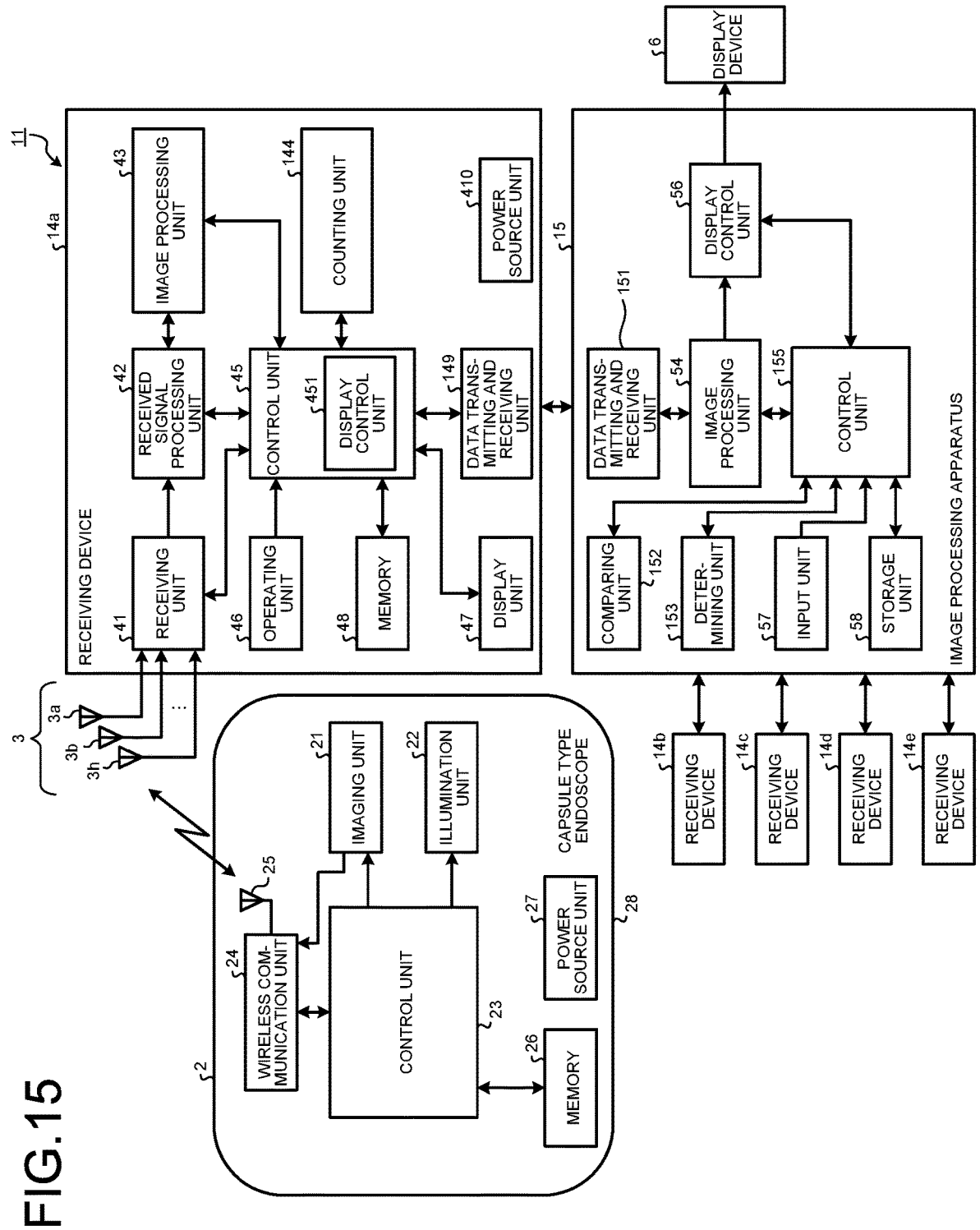
FIG. 15 is a block diagram illustrating a configuration of the capsule type endoscope system illustrated in FIG. 14.

FIG. 15 is a block diagram illustrating a configuration of the capsule type endoscope system illustrated in FIG. 14. A counting unit 144 of the receiving device 14a sequentially extracts images of interest from images generated by the image processing unit 43, and counts the number of images of interest extracted. The counting unit 144 is formed of a processor, such as a CPU.

A data transmitting and receiving unit 149 of the receiving device 14a is wirelessly communicatable with the image processing apparatus 15, and sequentially transmits images, the number of images of interest, and related information, to the image processing apparatus 15. The data transmitting and receiving unit 149 is formed of a communication I/F, such as a wireless LAN.

The receiving devices 14b to 14e may be configured similarly to the receiving device 14a. Further, the receiving devices 14b to 14e respectively receive, via receiving antenna units attached to different subjects, wireless signals transmitted from capsule type endoscopes inserted in those subjects, but illustration for this reception is omitted in FIG. 14.

A data transmitting and receiving unit 151 of the image processing apparatus 15 is wirelessly communicatable with each of the receiving devices 14a to 14e, and sequentially receive images, the number of images of interest, and related information, from each of the receiving devices 14a to 14e. The data transmitting and receiving unit 151 is an interface that is connectable to a communication line, such as a wireless LAN.

A comparing unit 152 of the image processing apparatus 15 compares the numbers of images of interest in image groups acquired by the receiving devices 14a to 14e, with one another. The comparing unit 152 is formed of a processor, such as a CPU.

A determining unit 153 of the image processing apparatus 15 determines, based on a result of the comparison by the comparing unit 152, priority of processing for transmission of the image groups to the image processing apparatus 15 from the receiving devices 14a to 14e. Specifically, the determining unit 153 determines, based on the result of the comparison by the comparing unit 152, that the image group having many images of interest has a high priority. The determining unit 153 is formed of a processor, such as a CPU.

A control unit 155 of the image processing apparatus 15 executes control of causing the receiving devices 14a to 14e to respectively transmit the image groups according to transmission rates based on the priority determined by the determining unit 153. The control unit 155 is formed of a processor, such as a CPU.

Figure 16:
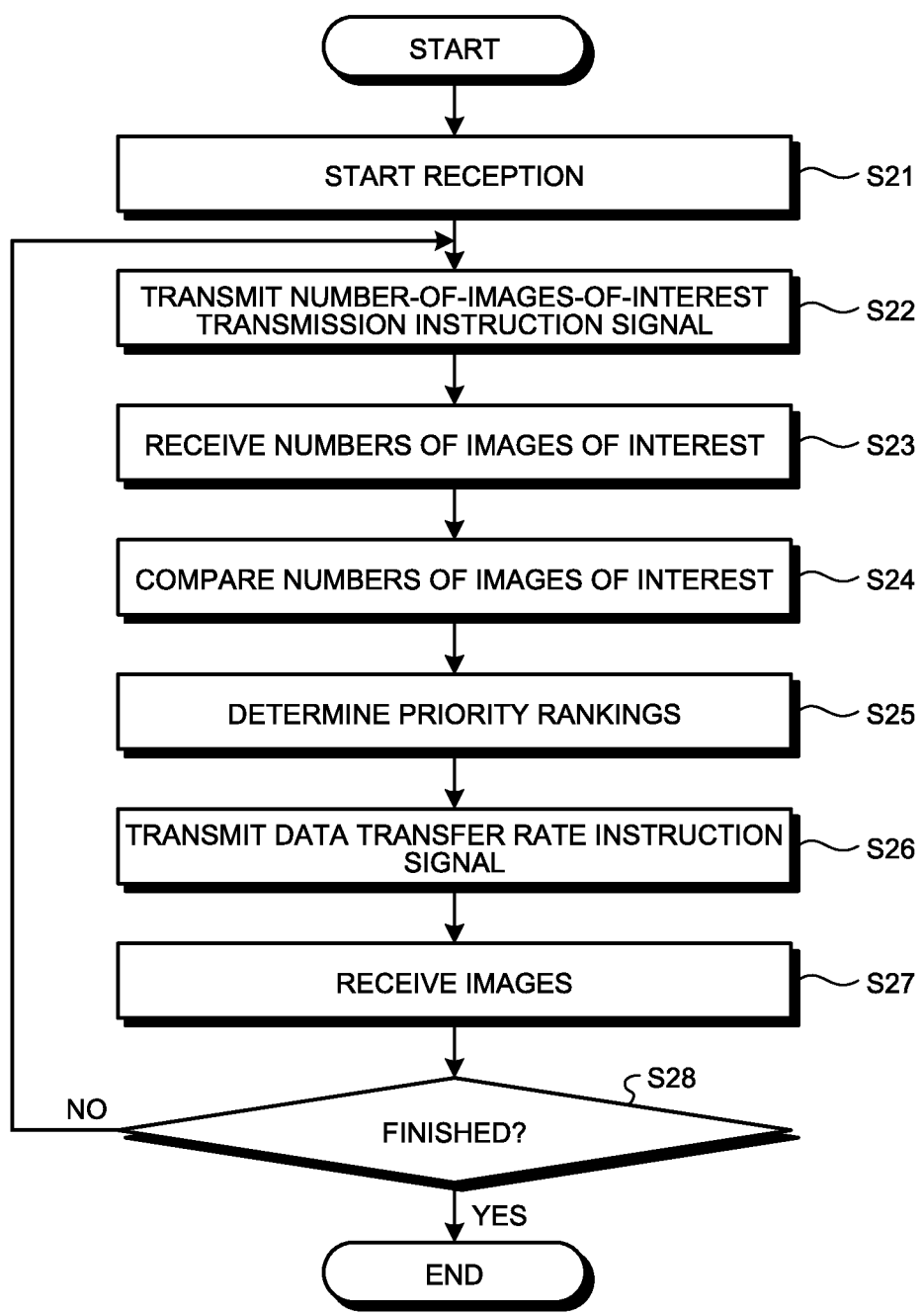
FIG. 16 is a flow chart illustrating a procedure of processing executed by an image processing apparatus illustrated in FIG. 15.
Figure 17:
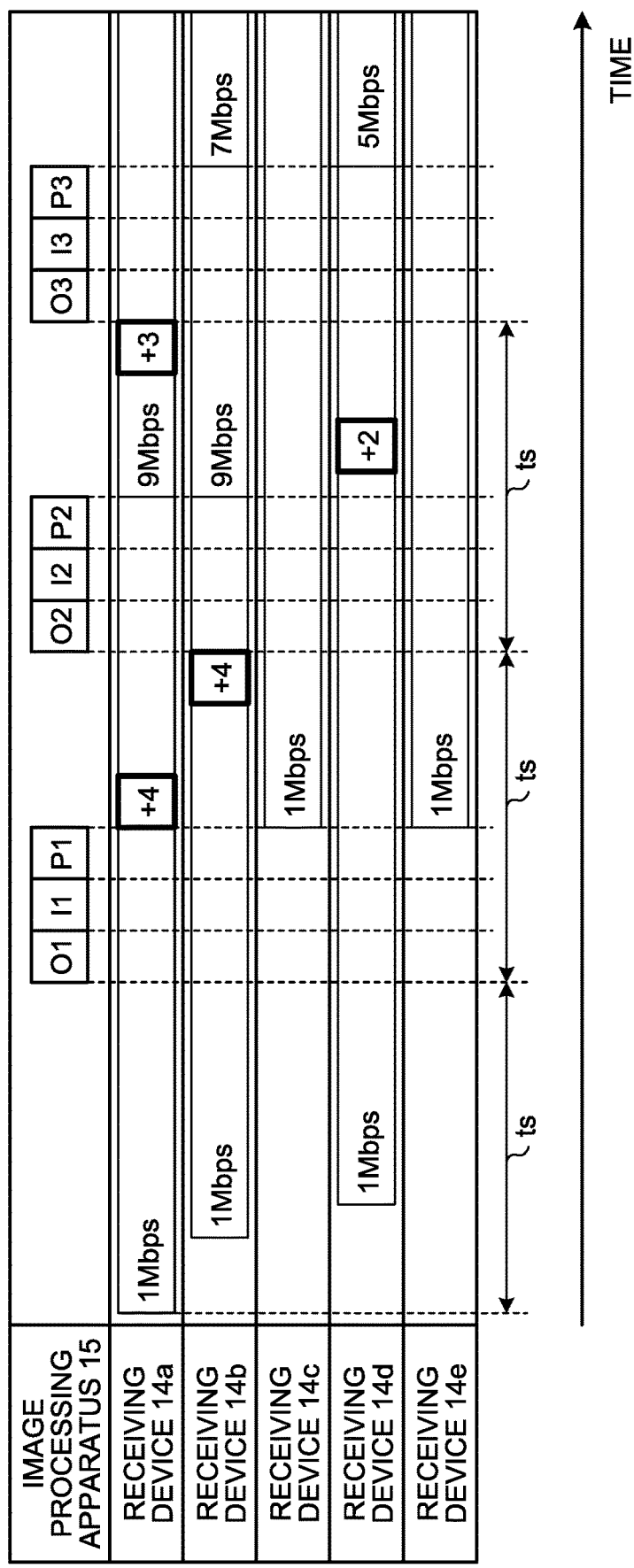
FIG. 17 is a diagram for explanation of the flow chart in FIG. 16.

Next, processing executed by the image processing apparatus 15 will be described. FIG. 16 is a flow chart illustrating a procedure of the processing executed by the image processing apparatus illustrated in FIG. 15. FIG. 17 is a diagram for explanation of the flow chart of FIG. 16. In FIG. 17, the numbers of images of interest extracted by the counting units of the receiving devices 14a to 14e are written in bold frames. As illustrated in FIG. 16 and FIG. 17, firstly, the image processing apparatus 15 starts receiving image data by wireless communication from a receiving device (Step S21). At first, images from the receiving device 14a are received. Further, images from the receiving device 14b and the receiving device 14d are received. Transmission rates of the wireless communication between: the image processing apparatus 15; and a receiving device 14, receiving device 14b, and receiving device 14d are 1 Mbps, which is the initial value.

When the wireless communication is started, the control unit 155 of the image processing apparatus 15 executes processing (O1) of transmitting a number-of-images-of-interest transmission instruction signal, per predetermined time interval is (Step S22).

The receiving device 14a, the receiving device 14b, and the receiving device 14d, which are wirelessly communicating with the image processing apparatus 15, receive the number-of-images-of-interest transmission instruction signal, and transmit the numbers of images of interest that have been counted up to this time point. The image processing apparatus 15 then executes processing (I1) of receiving the numbers of images of interest from the receiving device 14a, the receiving device 14b, and the receiving device 14d (Step S23). Specifically, as illustrated in FIG. 17, at the time of the processing (I1), extraction of images of interest represented by a bold frame is not being executed in any of the receiving devices, and thus the image processing apparatus 15 receives the numbers of images of interest from these receiving devices as zero.

The comparing unit 152 then compares the numbers of images of interest received from the receiving device 14a, the receiving device 14b, and the receiving device 14d, with one another (Step S24).

Further, based on a result of the comparison by the comparing unit 152, the determining unit 153 executes processing (P1) of determining priority of processing for transmission of images to the image processing apparatus 15 from the receiving device 14a, the receiving device 14b, and the receiving device 14d (Step S25). Since the numbers of images of interest from the receiving device 14a, the receiving device 14b, and the receiving device 14d are all zero, their priorities are the same.

FIG. 18 is a diagram illustrating correspondence between priority and transmission rates. As illustrated in FIG. 18, the transmission rate corresponding to the first priority is 9 Mbps, the transmission rate corresponding to the second priority is 7 Mbps, the transmission rate corresponding to the third priority is 5 Mbps, the transmission rate corresponding to the fourth priority is 3 Mbps, the transmission rate corresponding to the fifth priority is 2 Mbps, and when the number of images of interest is zero, the transmission rate is at the initial value, 1 Mbps. As a result, the control unit 155 executes control of causing the receiving device 14a, the receiving device 14b, and the receiving device 14d to transmit images still at the transmission rate of 1 Mbps. Specifically, the control unit 155 transmits a data transfer rate instruction signal causing the receiving device 14a, the receiving device 14b, and the receiving device 14d to execute transmission at the transmission rate of 1 Mbps (Step S26).

Thereafter, the image processing apparatus 15 receives image data (Step S27).

The control unit 155 then determines whether or not the transfer of images has finished (Step S28), and if the control unit 155 determines that the transfer has not finished (Step S28: No), the control unit 155 returns to Step S22.

Thereafter, as illustrated in FIG. 17, images from the receiving device 14c and a receiving device 15e are received. Transmission rates of the wireless communication of the receiving device 14c and the receiving device 14e then are at 1 Mbps, the initial value. Further, it is now assumed that four images of interest have been detected in each of the receiving device 14a and the receiving device 14b (as written "+4" in the bold frames in FIG. 17).

When a predetermined time interval is has elapsed from the processing (O1), the control unit 155 of the image processing apparatus 15 executes processing (O2) of transmitting a number-of-images-of-interest transmission instruction signal again (Step S22).

The receiving devices 14a to 14e, which are wirelessly communicating with the image processing apparatus 15, receive the number-of-images-of-interest transmission instruction signal, and transmit the numbers of images of interest. The image processing apparatus 15 then executes processing (I2) of receiving the numbers of images of interest from the receiving devices 14a to 14e (Step S23).

The comparing unit 152 then compares the numbers of images of interest received from the receiving devices 14a to 14e, with one another (Step S24).

Further, based on a result of the comparison by the comparing unit 152, the determining unit 153 executes processing (P2) of determining priority of processing for transmission of images to the image processing apparatus 15 from the receiving devices 14a to 14e (Step S25). Since the numbers of images of interest from the receiving device 14a and receiving device 14b are four, while the numbers of images of interest from the receiving device 14c, receiving device 14d, and the receiving device 14e are zero; the priority of the receiving device 14a and the receiving device 14b are determined to be higher.

As a result, as illustrated in FIG. 18, the control unit 155 transmits a data transfer rate instruction signal causing the receiving device 14a and 14b to transmit images at the transmission rate of 9 Mbps, and the receiving devices 14c to 14e to transmit images still at the transmission rate of 1 Mbps (Step S26).

Thereafter, the image processing apparatus 15 receives the images (Step S27).

The control unit 155 then determines whether or not the transfer of images has finished (Step S28), and if the control unit 155 determines that the transfer has not finished (Step S28: No), the control unit 155 returns to Step S22.

It is now assumed that, thereafter, as illustrated in FIG. 17, three images of interest in the receiving device 14a, and two images of interest in the receiving device 14d have been detected (as written, "+3" and "+2", in the bold frames in FIG. 17).

When a predetermined time interval is has elapsed from the processing (O2), the control unit 155 of the image processing apparatus 15 executes processing (O3) of transmitting a number-of-images-of-interest transmission instruction signal again (Step S22).

The receiving devices 14a to 14e that are wirelessly communicating with the image processing apparatus 15 receive the number-of-images-of-interest transmission instruction signal, and transmit the numbers of images of interest. The image processing apparatus 15 then executes processing (I3) of receiving the numbers of images of interest from the receiving devices 14a to 14e (Step S23).

The comparing unit 152 then compares the numbers of images of interest received from the receiving devices 14a to 14e, with one another (Step S24).

Further, based on a result of the comparison by the comparing unit 152, the determining unit 153 executes processing (P3) of determining priority of processing for transmission of images to the image processing apparatus 15 from the receiving devices 14a to 14e (Step S25). The priorities are in the order of: the receiving device 14a (the number of images of interest being seven); the receiving device 14b (the number of images of interest being four); the receiving device 14d (the number of images of interest being two); and the receiving device 14c and receiving device 14e (the numbers of images of interest being zero).

As a result, the control unit 155 transmits a data transfer rate instruction signal causing, as illustrated in FIG. 18, the receiving device 14a to transmit image data of the image group still at the transmission rate of 9 Mbps, the receiving device 14b at the transmission rate of 7 Mbps, the receiving device 14d at the transmission rate of 5 Mbps, and the receiving devices 14c and 14e still at the transmission rate of 1 Mbps (Step S26).

Thereafter, the image processing apparatus 15 receives the images (Step S27).

The control unit 155 then determines whether or not the transfer of images has finished (Step S28), and if the control unit 155 determines that the transfer has not finished (Step S28: No), the control unit 155 returns to Step S22. Thereafter, the above described series of processing is repeated until the transfer of images is finished.

As described above, according to the second embodiment, since an image group, from which many images of interest have been detected, is preferentially transferred, a user is able to observe image groups in descending order of priority.

Modified Examples 2-1

Figure 19:
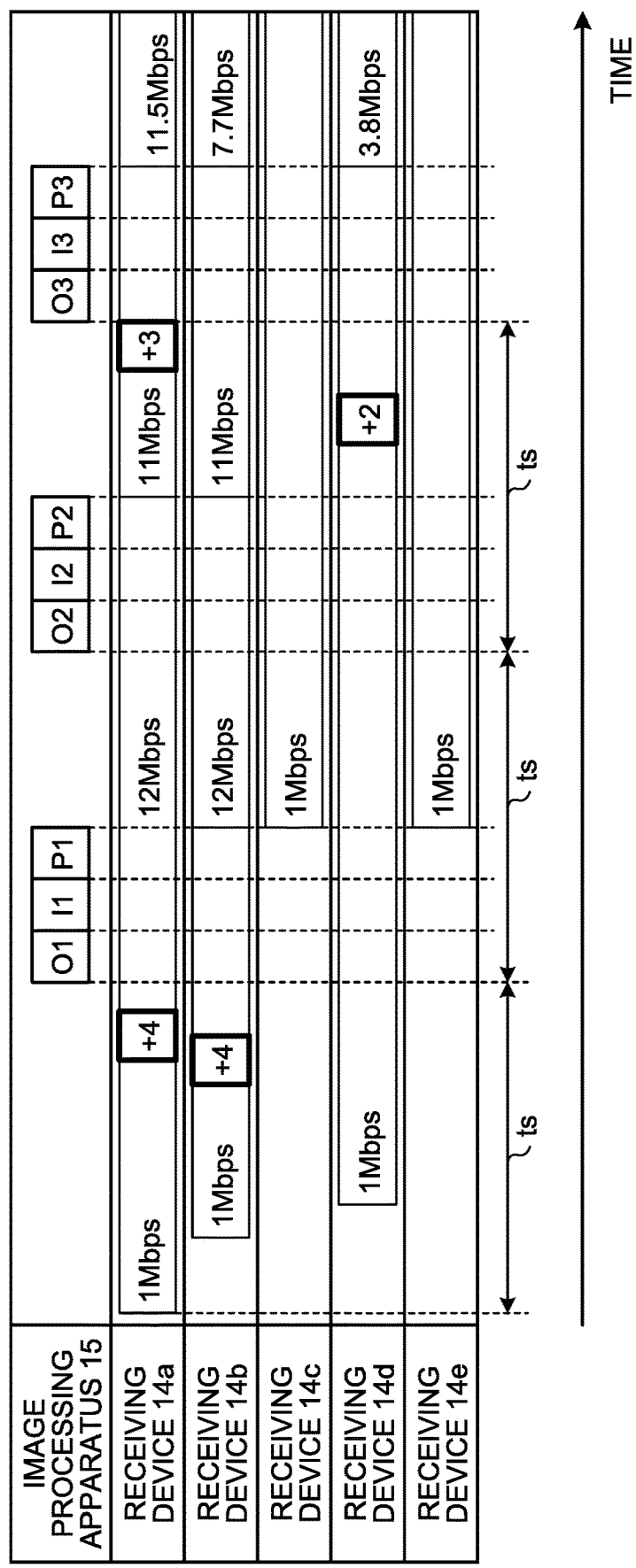
FIG. 19 is a diagram for explanation of processing executed by an image processing apparatus according to a modified example 2-1 of the second embodiment.

FIG. 19 is a diagram for explanation of processing executed by an image processing apparatus according to a modified example 2-1 of the second embodiment. As illustrated in FIG. 19, in the modified example 2-1, transmission rates from the receiving devices 14a to 14e to the image processing apparatus 15 are assigned such that a total of these transmission rates becomes 25 Mbps at most. For example, in the processing (P3) for determination of the priority, the control unit 155 sets the transmission rates of the receiving device 14c and the receiving device 14e with zero images of interest at 1 Mbps. Further, the remaining 23 Mbps are assigned to the other receiving devices. The transmission rate of the receiving device 14a having the first priority is set at 23 Mbps×3/6=11.5 Mbps, the transmission rate of the receiving device 14b having the second priority is set at 23 Mbps×2/6=7.7 Mbps, and the transmission rate of the receiving device 14d having the third priority is set at 23 Mbps×1/6=3.8 Mbps. As described above, if speed of data transfer has an upper limit, transmission rates may be assigned according to priority.

Modified Examples 2-2

Figure 20:
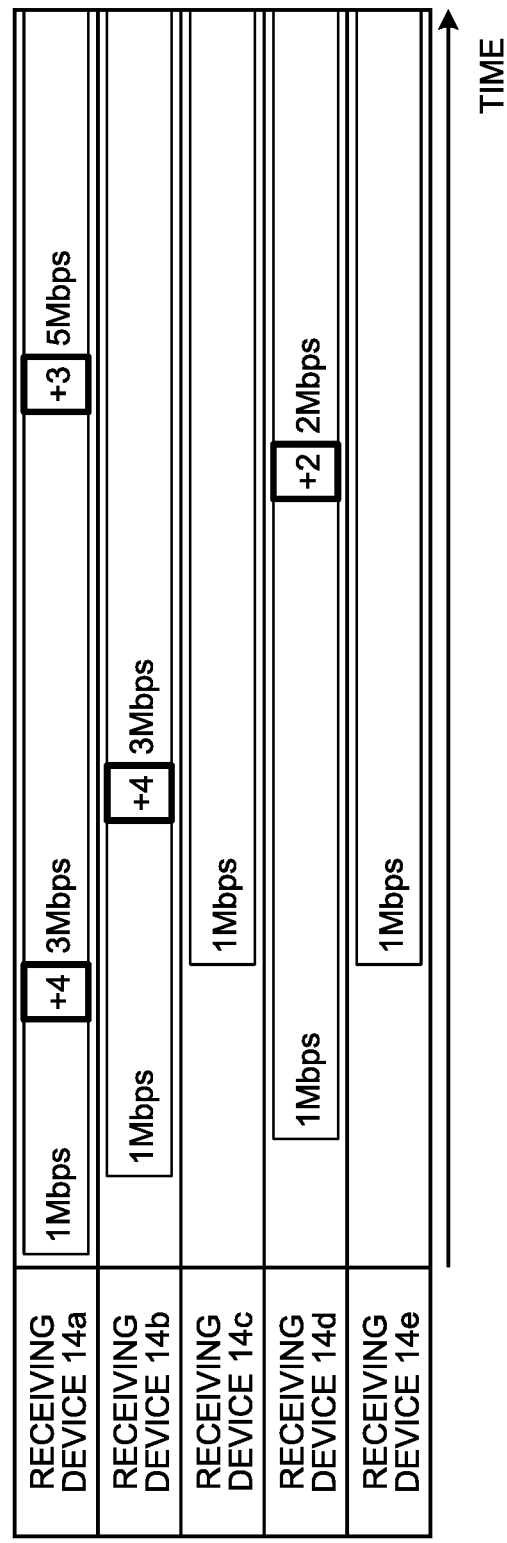
FIG. 20 is a diagram for explanation of processing executed by an image processing apparatus according to a modified example 2-2 of the second embodiment.

FIG. 20 is a diagram for explanation of processing executed by receiving devices according to a modified example 2-2 of the second embodiment. As illustrated in FIG. 20, in the modified example 2-2, when the receiving devices detect images of interest, the receiving devices increase their own transmission rates according to the numbers of images of interest. Specifically, the transmission rate of the receiving device 14a in the initial state is 1 Mbps; and the receiving device 14a increases the transmission rate to 2 Mbps when the number of images of interest is one or more, the receiving device 14a increases the transmission rate to 3 Mbps when the number of images of interest is four or more, and the receiving device 14a increases the transmission rate to 5 Mbps when the number of images of interest is seven or more. As described above, the receiving devices may be configured to change their own transmission rates.

Modified Examples 2-3

Figure 21:
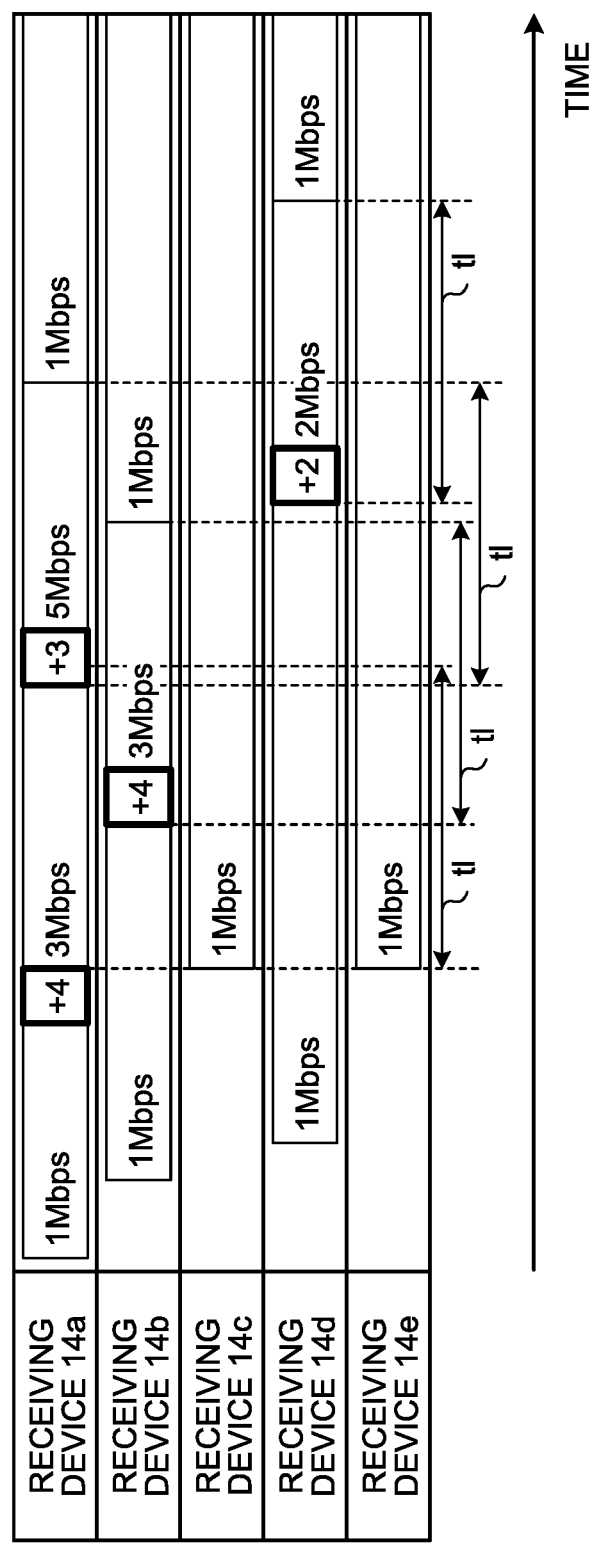
FIG. 21 is a diagram for explanation of processing executed by an image processing apparatus according to a modified example 2-3 of the second embodiment.

FIG. 21 is a diagram for explanation of processing executed by receiving devices according to a modified example 2-3 of the second embodiment. As illustrated in FIG. 21, the modified example 2-3 is also configured such that the receiving devices change their own transmission rates, similarly to the modified example 2-2. When each receiving device detects images of interest, the receiving device increases its own transmission rate according to the number of images of interest. The receiving device is also configured to automatically decrease its own transmission rate to 1 Mbps; if, after elapse of a predetermined time period t1 from the detection of the images of interest, no images of interest have been detected. Specifically, the transmission rate of the receiving device 14a in the initial state is 1 Mbps; and the receiving device 14a increases the transmission rate to 2 Mbps when the number of images of interest detected until a predetermined time period t1 elapses is one or more, the receiving device 14a increases the transmission rate to 3 Mbps when the number of images of interest detected then is four or more, and the receiving device 14a increases the transmission rate to 5 Mbps when the number of images of interest detected then is seven or more. In FIG. 21, when four images of interest are detected, the transmission rate is increased to 3 Mbps, and when three more images of interest are detected before elapse of a predetermined time period t1, the transmission rate is increased to 5 Mbps. Thereafter, since the receiving device 14a does not detect any images of interest even after elapse of a predetermined time period t1, the receiving device 14a decreases the transmission rate to 1 Mbps.

With respect to the above described embodiments, configurations for execution of processing on image groups from plural receiving devices based on priority according to the numbers of images of interest have been described, but the embodiments are not limited to these configurations. For example, there may be image groups classified by organ (the esophagus, the stomach, the small intestine, the large intestine, and the like) captured by one receiving device, and processing on these image groups may be executed based on priority according to the numbers of images of interest.

Further, with respect to each of the above described embodiments, a configuration for transmission of data of the numbers of images of interest and image groups to an image processing apparatus from receiving devices has been described, but the embodiments are not limited to this configuration. A configuration, in which data of the number of images of interest and image groups are transmitted from receiving devices to a server, and an image processing apparatus reads the data from the server, may be adopted. This server may be a server placed at a remote location connected via a network.

According to some embodiments, an image processing apparatus, an image processing system, an operation method of the image processing apparatus, and an operation program for the image processing apparatus, which enable users to observe image groups in descending order of priority, are able to be realized.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus configured to acquire a first image group and a second image group and execute image processing on the first and second image groups, the image processing apparatus comprising:
a processor comprising hardware, wherein the processor is configured to:
compare the number of images of interest in the first image group, with the number of images of interest in the second image group; and
determine, based on a result of the comparison, priority of processing on the first image group and processing on the second image group.

2. The image processing apparatus according to claim 1, wherein
the first image group is images acquired by a first receiving device, and
the second image group is images acquired by a second receiving device.

3. The image processing apparatus according to claim 2, wherein
the processor is further configured to:
determine, based on a result of the comparison, priority of processing for transmission of the first image group to the image processing apparatus from the first receiving device and processing for transmission of the second image group to the image processing apparatus from the second receiving device; and
execute control of causing the first receiving device and the second receiving device to respectively transmit the first image group and the second image group, based on the determined priority.

4. The image processing apparatus according to claim 2, wherein
the processor is further configured to:
determine, based on a result of the comparison, priority of processing for transmission of the first image group to the image processing apparatus from the first receiving device and processing for transmission of the second image group to the image processing apparatus from the second receiving device; and
execute control of causing the first receiving device and the second receiving device to respectively transmit the first image group and the second image group, according to transmission rates that are based on the determined priority.

5. The image processing apparatus according to claim 1, wherein
the processor is further configured to:
determine, based on a result of the comparison, priority of image processing to be executed on the first image group and image processing to be executed on the second image group;
execute image processing on each of the first image group and the second image group; and
execute control of executing the image processing on the first image group and the image processing on the second image group, based on the determined priority.

6. The image processing apparatus according to claim 1, wherein the images of interest include at least one of:
a red image having a large red color component;
a lesion image where a lesion has been detected;
a feature data detection image having predetermined feature data calculated from the image, the predetermined feature data being included in a predetermined range;
a captured image captured by a user; and
a selected image selected by a user.

7. The image processing apparatus according to claim 1, wherein the processor is configured to set the priority of the processing on one of the first image group and the second image group higher, the one having the larger number of images of interest.

8. An image processing system, comprising:
the image processing apparatus according to claim 2;
the first receiving device configured to acquire the first image group and transmit the first image group to the image processing apparatus; and
the second receiving device configured to acquire the second image group and transmit the second image group to the image processing apparatus.

9. An operation method of an image processing apparatus configured to acquire a first image group and a second image group and execute image processing on the first and second image groups, the operation method comprising:
comparing the number of images of interest in the first image group with the number of images of interest in the second image group; and
determining, based on a result of the comparison, priority of processing on the first image group and processing on the second image group.

10. A non-transitory computer-readable recording medium with an executable program stored thereon, the program operating an image processing apparatus configured to acquire a first image group and a second image group and execute image processing on the first and second image groups, the operation program causing the image processing apparatus to execute:
comparing the number of images of interest in the first image group with the number of images of interest in the second image group; and
determining, based on a result of the comparison, priority of processing on the first image group and processing on the second image group.

* * * * *